(12) United States Patent
Feng et al.

(10) Patent No.: US 10,059,806 B2
(45) Date of Patent: Aug. 28, 2018

(54) AMINOSILOXANE POLYMER AND METHOD OF FORMING

(71) Applicant: Dow Corning Corporation, Midland, MI (US)

(72) Inventors: Qian Feng, Midland, MI (US); Michael Salvatore Ferritto, Midland, MI (US); Patrick J. Fryfogle, Midland, MI (US); Bethany K. Johnson, Midland, MI (US); Kimmai Thi Nguyen, Midland, MI (US); Brett Lee Zimmerman, Frankenmuth, MI (US); Kenneth Edward Zimmerman, Midland, MI (US)

(73) Assignee: Dow Silicones Corporation, Midland, MI (US)

( * ) Notice: Subject to any disclaimer, the term of this patent is extended or adjusted under 35 U.S.C. 154(b) by 0 days.

(21) Appl. No.: 15/311,653

(22) PCT Filed: May 20, 2015

(86) PCT No.: PCT/US2015/031767
§ 371 (c)(1),
(2) Date: Nov. 16, 2016

(87) PCT Pub. No.: WO2015/179512
PCT Pub. Date: Nov. 26, 2015

(65) Prior Publication Data
US 2017/0096533 A1    Apr. 6, 2017
US 2018/0066113 A9    Mar. 8, 2018

Related U.S. Application Data

(60) Provisional application No. 62/001,415, filed on May 21, 2014, provisional application No. 62/001,421, (Continued)

(51) Int. Cl.
*C11D 3/37*    (2006.01)
*A61K 8/898*   (2006.01)
(Continued)

(52) U.S. Cl.
CPC ............... *C08G 77/26* (2013.01); *A61K 8/06* (2013.01); *A61K 8/898* (2013.01); *A61Q 5/12* (2013.01);
(Continued)

(58) Field of Classification Search
None
See application file for complete search history.

(56) References Cited

U.S. PATENT DOCUMENTS 2,798,053 A    7/1957   Brown
3,597,268 A    8/1971   Smith
(Continued)

FOREIGN PATENT DOCUMENTS

AU    B5243590 B    4/1990
CA    2274040 A1    11/2000
(Continued)

OTHER PUBLICATIONS

Machine Assisted Translation of JPH10158150A obtained from https://www4.j-platpat.inpit.go.jp on Oct. 4, 2017, 12 pages.
(Continued)

*Primary Examiner* — Ernst V Arnold
*Assistant Examiner* — Kyung Sook Chang
(74) *Attorney, Agent, or Firm* — Warner Norcross & Judd LLP

(57) ABSTRACT

An aminosiloxane polymer includes at least one Si-bonded functional group. This functional group has the chemical formula: $-(R-NH)_aR^1-N(R^2)-CH(-COOH)(-R^3-C(=O)-NR^4{}_2)$ (I). In Formula (I), R is a $C_1$-$C_{10}$ hydrocarbon group. $R^1$ is a $C_1$-$C_{10}$ hydrocarbon group. $R^2$ is a (Continued)

hydrogen atom, a $C_1$-$C_{12}$ hydrocarbon group, or a phenyl group. $R^3$ is a $C_1$-$C_4$ hydrocarbon group. Each $R^4$ is independently a hydrogen atom, a $C_1$-$C_{12}$ hydrocarbon group, a $C_1$-$C_{12}$ hydroxyl-hydrocarbon group, or a phenyl group. Moreover, "a" is 0 or 1, such that (R—NH) is optional. The aminosiloxane polymer can be formed using the method of this disclosure and can be formed in, and/or included in, the emulsion of this disclosure.

20 Claims, 2 Drawing Sheets

Related U.S. Application Data filed on May 21, 2014, provisional application No. 62/001,427, filed on May 21, 2014.

(51) Int. Cl.
- A61Q 5/12 (2006.01)
- C08G 77/26 (2006.01)
- C08L 83/08 (2006.01)
- A61K 8/06 (2006.01)
- C11D 3/00 (2006.01)
- C11D 17/00 (2006.01)

(52) U.S. Cl.
CPC ............ C08L 83/08 (2013.01); C11D 3/0015 (2013.01); C11D 3/373 (2013.01); C11D 17/0017 (2013.01)

(56) References Cited

U.S. PATENT DOCUMENTS

| | | | |
|---|---|---|---|
| 3,958,581 A | 5/1976 | Abegg et al. |
| 3,962,418 A | 6/1976 | Birkofer |
| 4,009,256 A | 2/1977 | Nowak, Jr. et al. |
| 4,070,152 A | 1/1978 | Pentz |
| 4,250,108 A | 2/1981 | Bouillon et al. |
| 4,290,974 A | 9/1981 | Bouillon et al. |
| 4,304,730 A | 12/1981 | Bouillon et al. |
| 4,311,626 A | 1/1982 | Ona et al. |
| 4,323,549 A | 4/1982 | Bouillon et al. |
| 4,327,031 A | 4/1982 | Bouillon et al. |
| 4,330,488 A | 5/1982 | Bouillon et al. |
| 4,387,089 A | 6/1983 | De Polo |
| 4,406,880 A | 9/1983 | Bouillon et al. |
| 4,489,057 A | 12/1984 | Welters et al. |
| 4,562,067 A | 12/1985 | Hopp et al. |
| 4,585,597 A | 4/1986 | Lang et al. |
| 4,704,272 A | 11/1987 | Oh et al. |
| 4,741,855 A | 5/1988 | Grote et al. |
| 4,775,526 A | 10/1988 | Lang et al. |
| 4,788,006 A | 11/1988 | Bolich, Jr. et al. |
| 5,391,400 A | 2/1995 | Yang |
| 5,399,652 A | 3/1995 | Bindl et al. |
| 5,643,557 A | 7/1997 | Eteve et al. |
| 5,690,915 A | 11/1997 | Eteve et al. |
| 5,690,917 A | 11/1997 | Eteve et al. |
| 5,695,747 A | 12/1997 | Forestier et al. |
| 5,708,070 A | 6/1998 | Joffre et al. |
| 5,762,912 A | 6/1998 | Eteve |
| 5,763,540 A | 6/1998 | Nakata et al. |
| 5,788,955 A | 8/1998 | Eteve et al. |
| 5,795,565 A | 8/1998 | Eteve et al. |
| 5,919,441 A | 7/1999 | Mendolia et al. |
| 5,976,557 A | 11/1999 | Friedrich et al. |
| 5,981,680 A | 11/1999 | Petroff et al. |
| 6,001,946 A | 12/1999 | Waldman et al. |
| 6,013,682 A | 1/2000 | Dalle et al. |
| 6,051,216 A | 4/2000 | Barr et al. |
| 6,124,490 A | 9/2000 | Gormley et al. |
| 6,171,516 B1 | 1/2001 | Inuzuka et al. |
| 6,248,855 B1 | 6/2001 | Dalle et al. |
| 6,277,445 B1 | 8/2001 | Hasegawa et al. |
| 6,329,462 B1 | 12/2001 | Hale et al. |
| 6,379,751 B1 | 4/2002 | Schäfer et al. |
| 6,437,042 B2 | 8/2002 | Kobayashi et al. |
| RE38,116 E | 5/2003 | Petroff et al. |
| 7,078,026 B2 | 7/2006 | Ferrari et al. |
| 8,455,603 B2 | 6/2013 | Ferenz et al. |
| 8,580,241 B2 | 11/2013 | Moriya |
| 8,940,282 B2 | 1/2015 | Seng et al. |
| 2003/0068348 A1 | 4/2003 | Ferrari et al. |
| 2003/0072730 A1 | 4/2003 | Tournilhac |
| 2003/0170188 A1 | 9/2003 | Ferrari et al. |
| 2003/0211057 A1 | 11/2003 | Majeti et al. |
| 2003/0235553 A1 | 12/2003 | Lu et al. |
| 2004/0180032 A1 | 9/2004 | Manelski et al. |
| 2006/0269506 A1 | 11/2006 | De Caire et al. |
| 2008/0254076 A1 | 10/2008 | Ferrari et al. |
| 2009/0183320 A1 | 7/2009 | Benabdillah |
| 2011/0039087 A1 | 2/2011 | Cauvin et al. |
| 2011/0052523 A1 | 3/2011 | Moriya et al. |
| 2011/0230633 A1 | 9/2011 | Ferenz et al. |
| 2012/0149930 A1 | 6/2012 | Moriya |
| 2017/0000722 A1 | 1/2017 | Feng et al. |

FOREIGN PATENT DOCUMENTS

| | | |
|---|---|---|
| EP | 0114607 A1 | 1/1983 |
| EP | 0487404 A1 | 5/1992 |
| EP | 0518772 A1 | 12/1992 |
| EP | 0518773 A1 | 12/1992 |
| EP | 0678292 A1 | 10/1995 |
| EP | 1266647 A1 | 12/2002 |
| EP | 1266648 A1 | 12/2002 |
| EP | 1266653 A1 | 12/2002 |
| FR | 2236515 A1 | 2/1975 |
| FR | 2282426 A2 | 3/1976 |
| FR | 2326405 A1 | 4/1977 |
| FR | 2430938 A1 | 2/1980 |
| FR | 2440933 A1 | 6/1980 |
| FR | 2592380 A1 | 7/1987 |
| FR | 2645148 A1 | 10/1990 |
| JP | H05320348 A | 12/1993 |
| JP | H07179479 A | 7/1995 |
| JP | H0790205 B2 | 10/1995 |
| JP | H08127657 A | 5/1996 |
| JP | H10158150 A | 6/1998 |
| JP | H10204144 A | 8/1998 |
| JP | 2000186149 A | 7/2000 |
| JP | 2001234071 A | 8/2001 |
| JP | 2001240679 A | 9/2001 |
| JP | 2004182680 A | 7/2004 |
| JP | 2006169130 A | 6/2006 |
| JP | 2007016156 A | 1/2007 |
| JP | 2007284359 A | 11/2007 |
| JP | 201146657 A | 3/2011 |
| JP | 2011511830 A | 4/2011 |
| JP | 2012126648 A | 7/2012 |
| JP | 201382819 A | 5/2013 |
| WO | WO9522311 A1 | 8/1995 |
| WO | WO9522331 A1 | 8/1995 |
| WO | 9840553 A1 | 9/1998 |
| WO | WO03101412 A2 | 12/2003 |
| WO | WO03105789 A1 | 12/2003 |
| WO | WO03105801 A1 | 12/2003 |
| WO | WO03106614 A2 | 12/2003 |
| WO | WO2004000247 A1 | 12/2003 |
| WO | WO2004054523 A1 | 7/2004 |
| WO | WO2004054524 A1 | 7/2004 |
| WO | WO2004060101 A2 | 7/2004 |
| WO | WO2004060271 A2 | 7/2004 |
| WO | WO2004060276 A2 | 7/2004 |
| WO | WO2015179011 A1 | 11/2015 |
| WO | WO2015179512 A1 | 11/2015 |
| WO | WO2015179513 A1 | 11/2015 |

(56) References Cited

FOREIGN PATENT DOCUMENTS

WO    WO2016014127 A1    1/2016
WO    WO2016014128 A1    1/2016

OTHER PUBLICATIONS

PCT/US2015/031767 International Search Report dated Sep. 10, 2015, 3 pages.
English language abstract and machine translation for FR2282426 (A2) extracted from http://worldwide.espacenet.com database on Aug. 26, 2016, 15 pages.
English language abstract and machine translation for FR2645148 (A1) extracted from http://worldwide.espacenet.com database on Aug. 31, 2016, 31 pages.
PCT/US2015/031768 International Search Report dated Sep. 10, 2015, 3 pages.
PCT/US2015/020640 International Search Report dated Jun. 3, 2015, 4 pages.
English language abstract and machine translation for JPH08127657 (A) extracted from http://worldwide.espacenet.com database on Dec. 4, 2017, 39 pages.
English language abstract and machine translation for JPH07179479 (A) extracted from http://worldwide.espacenet.com database on Dec. 12, 2017, 14 pages.
English language abstract and machine translation for JP2004182680 (A) extracted from http://worldwide.espacenet.com database on Dec. 12, 2017, 16 pages.
English language abstract and machine translation for JP2006169130 (A) extracted from http://worldwide.espacenet.com database on Dec. 12, 2017, 14 pages.
English language abstract and machine translation for JP2007016156 (A) extracted from http://worldwide.espacenet.com database on Dec. 12, 2017, 22 pages.
English language abstract and machine translation for JP2007284359 (A) extracted from http://worldwide.espacenet.com database on Dec. 12, 2017, 21 pages.
English language abstract and machine translation for JPH0790205 (B2) extracted from http://worldwide.espacenet.com database on Dec. 12, 2017, 12 pages.

AMINOSILOXANE POLYMER AND METHOD OF FORMING

CROSS-REFERENCE TO RELATED APPLICATIONS

This application is the National Stage of International Application No. PCT/US2015/031767 filed on 20 May 2015, which claims priority to and all advantages of U.S. Appl. No. 62/001,415 filed on 21 May 2014, U.S. Appl. No. 62/001,421 filed on 21 May 2014, and U.S. Appl. No. 62/001,427 filed on 21 May 2014, the contents of which are hereby incorporated by reference.

FIELD OF THE INVENTION

This disclosure generally relates to an aminosiloxane polymer that includes at least one Si-bonded functional group having a particular chemical formula. This disclosure also provides a method of forming the aminosiloxane polymer.

BACKGROUND OF THE INVENTION

In both fabric/textile compositions and in personal care compositions, softening of substrates can be desirable. However, in the current marketplace, the softening of substrates can be difficult to accomplish and can be quite temporary. Moreover, there are many ways known in the art to soften fabrics and textiles, and many ways to soften human hair. However, all of these are also temporary and can be expensive. Accordingly, there remains an opportunity for improvement.

BRIEF SUMMARY OF THE INVENTION

This disclosure provides an aminosiloxane polymer including at least one Si-bonded functional group. This functional group has the chemical formula:

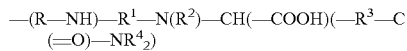

In Formula (I), R is a $C_1$-$C_{10}$ hydrocarbon group. $R^1$ is a $C_1$-$C_{10}$ hydrocarbon group. $R^2$ is a hydrogen atom, a $C_1$-$C_{12}$ hydrocarbon group, or a phenyl group. $R^3$ is a $C_1$-$C_4$ hydrocarbon group. Each $R^4$ is independently a hydrogen atom, a $C_1$-$C_{12}$ hydrocarbon group, a $C_1$-$C_{12}$ hydroxyl-hydrocarbon group, or a phenyl group. Moreover, "a" is 0 or 1, such that (R—NH) is optional. This disclosure also provides a method of forming the aminosiloxane polymer and an emulsion that includes the aminosiloxane polymer.

BRIEF DESCRIPTION OF THE DRAWINGS

Other advantages of the present disclosure will be readily appreciated, as the same becomes better understood by reference to the following detailed description when considered in connection with the accompanying drawings wherein.

DETAILED DESCRIPTION

Figure 1:
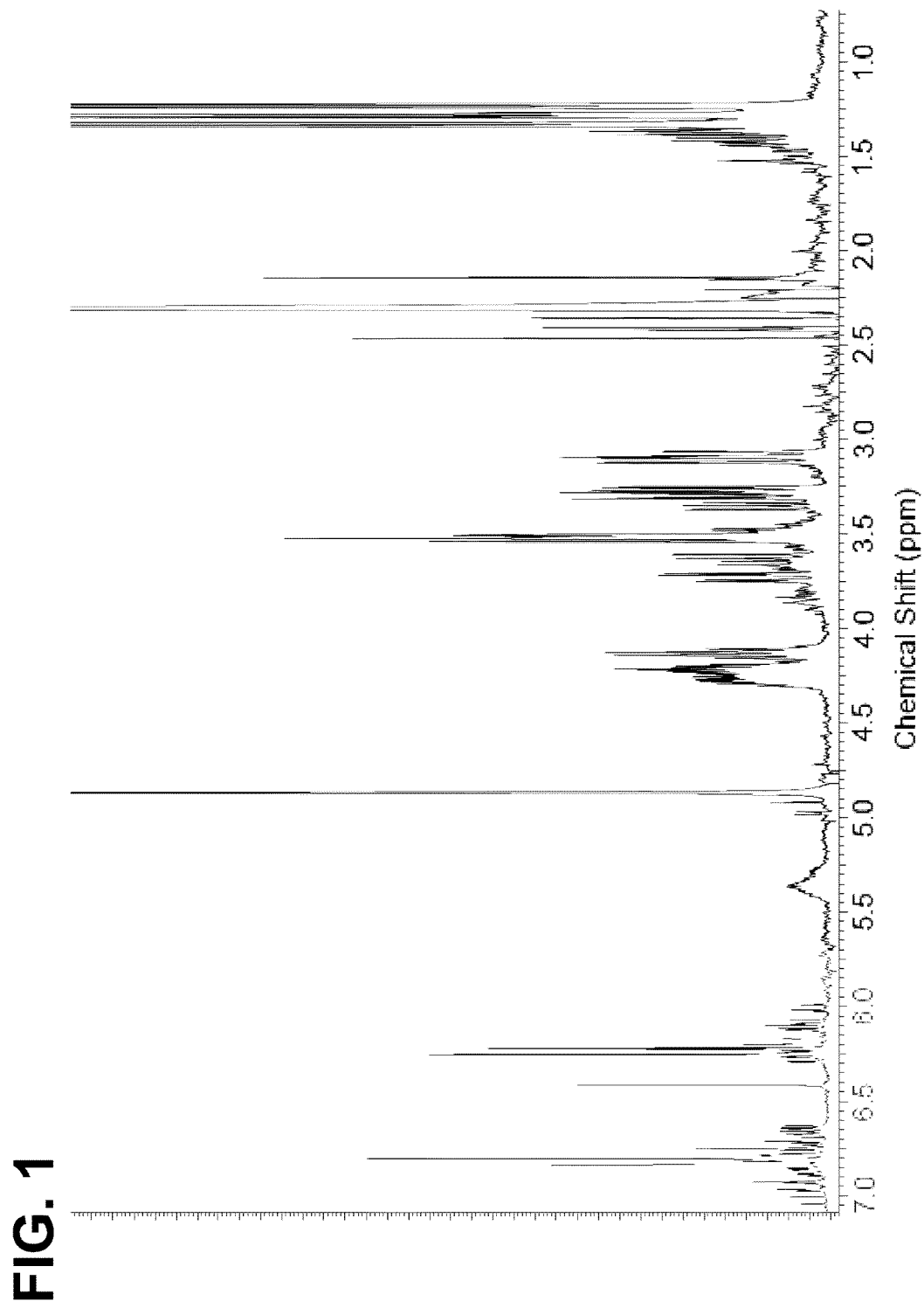
FIG. 1 is a $^1$H NMR spectrograph of Example 1.

This disclosure provides an aminosiloxane polymer including at least one Si-bonded functional group. This functional group has the chemical formula:

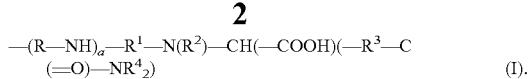

In Formula (I), R is a $C_1$-$C_{10}$ hydrocarbon group. $R^1$ is a $C_1$-$C_{10}$ hydrocarbon group. $R^2$ is a hydrogen atom, a $C_1$-$C_{12}$ hydrocarbon group, or a phenyl group. $R^3$ is a $C_1$-$C_4$ hydrocarbon group. Each $R^4$ is independently a hydrogen atom, a $C_1$-$C_{12}$ hydrocarbon group, a $C_1$-$C_{12}$ hydroxyl-hydrocarbon group, or a phenyl group.

Examples of R include a methyl, ethyl, or propyl group, or any hydrocarbon group having up to 10 carbon atoms. R can have 1, 2, 3, 4, 5, 6, 7, 8, 9, or 10 carbon atoms or any range of values therebetween. Hydrocarbons can include saturated hydrocarbons, unsaturated hydrocarbons having one or more double or triple bonds between carbon atoms, cycloalkanes having one or more carbon rings to which hydrogen atoms are attached, or aromatic hydrocarbons. Moreover, "a" is 0 or 1, such that (R—NH) is optional, i.e., if "a" is 0, then (R—NH) is not present. In one embodiment, "a" is 1. In another embodiment, "a" is 0.

$R^1$ may be any of the groups described above relative to R and may be independently chosen from R, i.e., R and $R^1$ may be the same or different from one another. In one embodiment, $R^2$ is a hydrogen atom. In another embodiment, $R^2$ is a $C_1$-$C_{12}$ hydrocarbon group that can have 1, 2, 3, 4, 5, 6, 7, 8, 9, 10, 11, or 12, carbon atoms or any range of values therebetween. The hydrocarbon group may be as described above. In another embodiment, $R^2$ is a phenyl group. $R^3$ is a $C_1$-$C_4$ hydrocarbon group that may be any as described above or may be different.

In one embodiment, each $R^4$ is independently a $C_1$-$C_{12}$ hydrocarbon group, such as those described above. In another embodiment, each $R^4$ is independently a $C_1$-$C_{12}$ hydroxyl-hydrocarbon group. The terminology "hydroxyl-hydrocarbon group" describes a hydrocarbon group, such as any one of those described above, wherein at least one of the hydrogen atoms is substituted with a hydroxyl group, i.e., an —OH group. The hydroxyl group may be located at any point in the hydrocarbon. In one embodiment, $R^4$ is an N-methyl glutamine group. In other embodiments, at least one or each of $R^4$ is a hydrogen atom. In other embodiments, at least one or each of $R^4$ is a phenyl group. In view of the foregoing, each $R^4$ may be the same as or different from each other.

In still other embodiments, $R^1$ is a $C_3$ hydrocarbon group, $R^2$ is a hydrogen atom, and $R^3$ is a $C_1$ hydrocarbon. Moreover, each $R^4$ may independently be a hydroxyl-hydrocarbon group. Still further, the Si-bonded functional group may have the chemical structure:

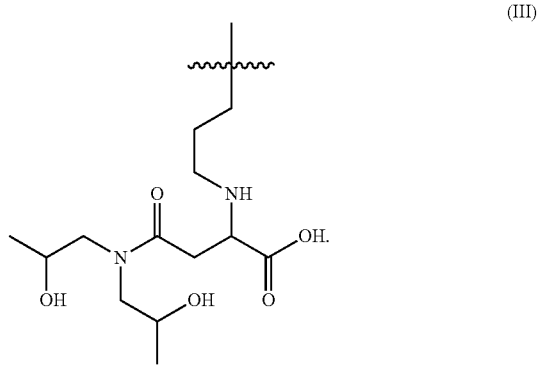 [SMILES: *CCCNC(CC(=O)N(CC(C)O)CC(C)O)C(=O)O]

In one embodiment, the aminosiloxane polymer is described as the reaction product of: (A) a polyorganosiloxane having an amino group; and (B) a reaction product of i) an alkylamine and/or alkanolamine, and ii) an alkenyl cyclic anhydride, such as maleic anhydride and/or itaconic anhydride. In another embodiment, the aminosiloxane polymer is described as the reaction product of: (A) the polyorganosiloxane having the amino group; and (B) the reaction product of i) an alkanolamine, and ii) an alkenyl cyclic anhydride. In still other embodiments, the aminosiloxane polymer is described as the reaction product of: (A) the polyorganosiloxane having the amino group; and (B) the reaction product of i) an alkylamine, and ii) an alkenyl cyclic anhydride. The alkenyl cyclic anhydride may be any known in the art. The aforementioned reactions may be alternatively described as (A)+(B)=aminosiloxane polymer. Said another way, the reaction product (B) is typically first formed and then reacted with (A). The alkylamine and/or alkanolamine may react with the alkenyl cyclic anhydride in the presence of (A) or in the absence of (A).

The (A) polyorganosiloxane having the amino group may be any in the art. For example, the polyorganosiloxane may include any M, D, T, and Q units. The symbols M, D, T, and Q represent the functionality of structural units of polyorganosiloxanes. M represents the monofunctional unit $R^0_3SiO_{1/2}$. D represents the difunctional unit $R^0_2SiO_{2/2}$. T represents the trifunctional unit $R^0SiO_{3/2}$. Q represents the tetrafunctional unit $SiO_{4/2}$. Generic structural formulas of these units are shown below:

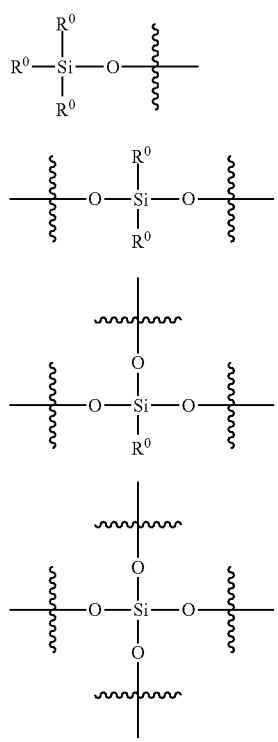

In these structures/formulae, each $R^0$ may be any hydrocarbon, aromatic, aliphatic, alkyl, alkenyl, or alkynl group. Similarly, the polyorganosiloxane is not particularly limited in molecular weight or viscosity and may be a fluid, gum, gel, etc.

In various embodiments, the polyorganosiloxane has the following chemical formula:

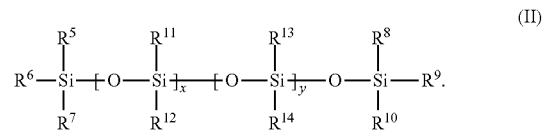

(II)

In Formula (II), each of $R^5$, $R^6$, $R^7$, $R^8$, $R^9$, $R^{10}$, $R^{11}$, $R^{12}$, and $R^{13}$ is independently OH, R'(OR")$_m$ or R'OH. Moreover, "m" is 1 to 3. Each of R' and R" is independently an alkyl group, a $C_1$-$C_{12}$ hydrocarbon group, a $C_2$-$C_{30}$ alkenyl group, a $C_6$-$C_{12}$ aromatic group, or a polyalkyleneoxy group. More specifically, any one or more of $R^5$-$R^{13}$ can independently have 1, 2, 3, 4, 5, 6, 7, 8, 9, 10, 11, or 12 carbon atoms and can independently be any one or more of the hydrocarbon groups, alkenyl groups, or aromatic groups described above or known in the art.

In various embodiments, at least one or each of $R^5$-$R^{13}$ is a methyl group. In other embodiments, at least one or each of $R^5$-$R^{13}$ is OH. In still other embodiments, at least one or each of $R^5$-$R^{13}$ is R'(OR")$_m$ where "m" is 1, 2, or 3 and each of R' and R" is independently an alkyl group. In further embodiments, at least one or each of $R^5$-$R^{13}$ is R'OH where R' is as described above. In another embodiment, at least one or each of $R^5$-$R^{13}$ is a hydrogen atom. In other embodiments, at least one or each of $R^5$-$R^{13}$ is independently a $C_2$-$C_{30}$ alkenyl group, alternatively a $C_2$-$C_{12}$ alkenyl group. In still other embodiments, at least one or each of $R^5$-$R^{13}$ is independently a $C_6$-$C_{12}$ aromatic group. In certain embodiments, at least one of $R^5$-$R^{13}$ is a phenyl group. In further embodiments, at least one or each of $R^5$-$R^{13}$ is independently a polyalkyleneoxy group. Polyalkyleneoxy groups may be alternatively described as alkylene oxide (AO) groups, such as an ethylene oxide (EO) groups, propylene oxide (PO) groups, butylene oxide (BO) groups, etc., or combinations thereof. In still other embodiments, examples of suitable AO groups that can be utilized include, but are not limited to, EO groups, PO groups, BO groups, amylene oxide groups, mixtures thereof, AO-tetrahydrofuran mixtures, epihalohydrins, and aralkylene styrenes, and combinations thereof. The structures of these compounds are known in the art. All combinations of the aforementioned groups are hereby expressly contemplated in various non-limiting embodiments.

In Formula (II), "x" can be from 1-3,000, 1-2,500, 1-2,000, 1-1,500, 1-1,000, 1-500, 1-100, 200-600, 250-550, 300-500, 350-450, or 400-450. Moreover, "y" can be from 1-100, 5-95, 10-90, 15-85, 20-80, 25-75, 30-70, 35-65, 40-60, 45-55, or 50-55. All values and ranges of values therebetween, and all combinations of these values, are hereby expressly contemplated in various non-limiting embodiments.

$R^{14}$ includes the amino group. The amino group is typically —NH or $NH_2$. However, the amino group may be NHR' where R' may be any alkyl group described above, e.g. having 1, 2, 3, 4, 5, 6, 7, 8, 9, 10, 11, or 12, or more, carbon atoms.

The amino group may be included in any pendant, internal, or terminal portion of a hydrocarbon, aromatic, aliphatic, alkyl, alkenyl, or alkynl group. For example, the amino group may be bonded to or within an alkyl group having 1, 2, 3, 4, 5, 6, 7, 8, 9, 10, 11, or 12 carbon atoms or any value or range of values therebetween. Moreover, $R^{14}$ may include a $NH_2$ or NH moiety bonded to a linear, branched, or cyclic hydrocarbon having 1-6 carbon atoms and the linear, branched, or cyclic hydrocarbon is bonded to a Si atom of the polyorganosiloxane of Formula (II). The amino group may include two or more $NH_2$, NH, and/or NHR' moieties. In one embodiment, the amino group has the chemical formula —$(CH_2)_aNH_2$ where "a" is from 1-6. In still other embodiments, the amino group includes one or more $NH_2$, NH, and/or NHR', moieties.

The alkylamine may be any known in the art. For example, the alkylamine may include an alkyl group and an amine group bonded together, e.g. an alkyl backbone and an amine group bonded to the backbone. The alkyl group may be any alkyl group in the art, e.g. an alkyl group having 1, 2, 3, 4, 5, 6, 7, 8, 9, 10, 11, or 12 (or up to 30) carbon atoms or may be any of the hydrocarbon groups described above. The amine group may also be any of the art. In one embodiment, the alkylamine includes at least one NH moiety and at least one carbon chain having 3-30 carbon atoms.

The alkanolamine may be any known in the art. Typically, alkanolamines include an alkyl group and a hydroxyl (e.g. alcohol) group bonded together, e.g. an alkyl backbone and hydroxyl group bonded to the backbone. The alkanolamine may include one, two, or at least two hydroxyl groups. In various embodiments, the alkanolamine includes one, two, or more than two NH, $NH_2$, or NHR' moieties and 2, 3, 4, or 5 hydroxyl groups. Various non-limiting examples of alkanolamines that may be utilized include diisopropanolamine, n-methyl glucamine, and combinations thereof.

The alkenyl cyclic anhydride is not particularly limited. In various embodiments, the alkenyl cyclic anhydride is chosen from maleic anhydride, itaconic anhydride, and combinations thereof. Maleic anhydride and itaconic anhydride have the following formulas and structures:

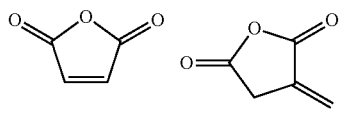

maleic anhydride
Chemical Formula:
$C_4H_2O_3$ itaconic anhydride
Chemical Formula:
$C_5H_4O_3$ Due to the symmetry of maleic anhydride, typically only one major product will be formed in the aforementioned reactions. However, when utilizing the asymmetrical itaconic anhydride, various major products may be formed, as is understood in the art and is shown in non-limiting example reaction schemes below. The amounts of the alkylamines, alkanolamines, alkenyl cyclic anhydride, and polyorganosiloxane having the amino group that are utilized herein are described in greater detail below relative to the method of forming the aminosiloxane polymer.

Referring back to the aminosiloxane polymer itself, this polymer may have any structure so long as it has an amino group (e.g. NH or $NH_2$ or NHR') and a siloxane backbone, e.g. a backbone including one or more M, D, T, and/or Q units, as described above. For example, the aminosiloxane polymer may have the chemical structure:

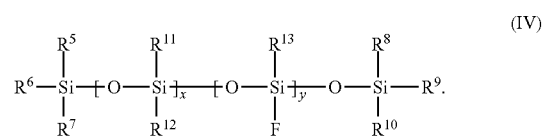

In Formula (IV), each of $R^5$, $R^6$, $R^7$, $R^8$, $R^9$, $R^{10}$, $R^{11}$, $R^{12}$, and $R^{13}$ is independently as described above. Moreover, "x" and "y" are also as described above. "F" represents the Si-bonded functional group, as described above. The aminosiloxane polymer may have a polysiloxane backbone having 2-10,000 silicone atoms or any value or range of values therebetween.

The weight or number average molecular weight of the aminosiloxane polymer is not particularly limited. Similarly, the degree of polymerization ("Dp") of the siloxane backbone of the aminosiloxane polymer is not particularly limited. In various embodiments, the Dp is from 2-5,000, 100-5,000, 100-4,500, 100-4,000, 100-3,500, 100-3,000, 100-2,500, 100-2,000, 100-1,500, 100-1,000, 100-500, or 100-250, alternatively from 200-1,000, 200-900, 200-800, 200-700, 200-600, 200-500, 200-400, or 200-300, alternatively from 250-550, 300-500, 350-450, or 400-450. Even further, the ratio of "x" and "y" of the siloxane backbone is not particularly limited. In various embodiments, the ratio is from 1-1,000, 100-500, or 100-250, alternatively from 200-1,000, 200-900, 200-800, 200-700, 200-600, or 200-500, alternatively from 40-300, 50-290, 60-280, 70-270, 80-260, 90-250, 100-240, 110-230, 120-220, 130-210, 140-200, 150-190, 160-180, or 160-170. All values and ranges of values therebetween the aforementioned values are hereby expressly contemplated in various non-limiting embodiments. Moreover, all combinations of the aforementioned embodiments are hereby expressly contemplated in various non-limiting embodiments.

This disclosure also provides an emulsion. The emulsion typically includes a liquid continuous phase and a dispersed phase that is dispersed in the continuous phase. The dispersed phase may be liquid, solid, gel, elastomer, rubber, etc. Alternatively, the emulsion may include a liquid continuous phase and a solid, gel, elastomer, or rubber dispersed phase and be more accurately described as a dispersion. However, for purposes of this disclosure, the terminology "dispersion" and "emulsion" are used interchangeably.

The dispersed phase of the emulsion typically includes, or is particles of, the aminosiloxane polymer. The aminosiloxane polymer may be present in the emulsion in an amount of from about 0.1-90, 10-70, or 15-60, parts by weight (pbw) per 100 pbw of the emulsion. In other embodiments, the aminosiloxane polymer is present in an amount of from about 5-90, 10-85, 15-80, 20-75, 25-70, 30-65, 35-60, 40-55, or 45-50, pbw per 100 pbw of the emulsion. All values and ranges of values therebetween the aforementioned values are hereby expressly contemplated in various non-limiting embodiments.

The terminology "particle" may refer to a single particle or a plurality of particles. Thus, the terminology "particle" and "particles" are used interchangeably herein. Typically, the particles are dispersed in the emulsion. In other words, the particles may be "dispersed particles." The particles themselves may be solids, gels, liquids, or combinations thereof. The particles are usually liquids or solids that are immiscible with, and dispersed in, a liquid continuous phase. The particles may include liquids as diluents, such that no external or additional liquids are added to the emulsion. Alternatively, the emulsion may include a liquid independent of any diluent.

The particles may be of varying sizes. In various embodiments, the emulsion includes particles having a size, e.g. by volume, from about 1 nm to 10 μm, of <1 μm, of from 1 nm to 1 μm, 100-1,000 nm, 10-200 nm, or 0.2-5 microns. In other embodiments, the emulsion includes particles having a size, e.g. by volume, from about 20-190, 30-180, 40-170, 50-160, 60-150, 70-140, 80-130, 90-120, or 100-110, nm. In still other embodiments, the emulsion includes particles having a size, e.g. by volume, of from about 0.3-4.9, 0.4-4.8, 0.5-4.7, 0.6-4.6, 0.7-4.5, 0.8-4.4, 0.9-4.3, 1-4.2, 1.1-4.1, 1.2-4, 1.3-3.9, 1.4-3.8, 1.5-3.7, 1.6-3.6, 1.7-3.5, 1.8-3.4, 1.9-3.3, 2-3.2, 2.1-3.1, 2.2-3, 2.3-2.9, 2.4-2.8, 2.5-2.7, or 2.5-2.6, microns. All values and ranges of values therebetween the aforementioned values are hereby expressly contemplated in various non-limiting embodiments.

In another embodiment, the emulsion may be classified as a nano-emulsion. The emulsion may include particles smaller or larger than the sizes described immediately above, depending on the desire of those of skill in the art. The particles typically have a dynamic viscosity of from about 10 to $1E^7$, or $1E^3$ to $1E^6$, cP, measured using a rheometer with an oscillation procedure (frequency sweep) of from $10^2$ to $10^{-3}$ Hz. However, the particles can have a dynamic viscosity outside of this range if desired. All values and ranges of values therebetween the aforementioned values are hereby expressly contemplated in various non-limiting embodiments.

In one embodiment, the emulsion includes a liquid (as the continuous phase) and the particles are dispersed in the liquid. Alternatively, the liquid may be an external liquid that is added independently of any other component. In one embodiment, the liquid is a non-polar liquid. In another embodiment, the liquid is a polar liquid, such as an alcohol or water. Typically, the liquid is water. The water may be tap water, well water, purified water, deionized water, and combinations thereof and may be present in the emulsion in varying amounts depending on the type of emulsion. In another embodiment, the emulsion includes a non-polar liquid (e.g., non-polar liquid particles) as the dispersed phase and a polar liquid as the continuous phase. In various embodiments, the liquid may be present in amounts of from about 20-80, 30-70, 40-60, or 50, pbw per 100 pbw of the emulsion, so long as a total amount of the emulsion does not exceed 100 pbw.

The emulsion may be further defined as a "colloid" or "colloid dispersion," terminology which can be used interchangeably. Typically, colloids include particles of <100 nanometers in size dispersed in the continuous phase. Colloids may be classified in numerous ways. The colloid may be reversible (i.e., exist in more than one state) or irreversible. Further, the colloid may be elastomeric or viscoelastic.

As is understood in the art, emulsions are typically classified into one of four categories according to a chemical nature of the dispersed and continuous phases. A first category is an oil-in-water (O/W) emulsion. O/W emulsions typically include a non-polar dispersed phase (e.g., oil) in an aqueous continuous phase (e.g. water) which forms particles. For purposes of the instant disclosure, the terminology "oil" includes non-polar molecules, may include any non-polar compound, and may include the particles of the disclosure. A second category of emulsion is a water-in-oil (W/O) emulsion. W/O emulsions typically include a polar dispersed phase, such as water or other hydrophilic substances or mixtures thereof, in a non-polar continuous phase, such as a hydrophobic oil or polymer. A third category is a water-in-oil-in-water (W/O/W) emulsion. These types of emulsions include a polar dispersed phase in a non-polar continuous phase which is, in turn, dispersed in a polar continuous phase. For example, W/O/W emulsions may include water droplets entrapped within larger oil droplets that in turn are dispersed in a continuous water phase. A fourth category is a water-in-water (W/W) emulsion. These types of emulsions include aqueous solvated molecules, e.g., particles of the disclosure, in a continuous aqueous solution wherein both the aqueous solvated molecules and the continuous aqueous solution include different molecules that are water-soluble. Without intending to be bound by any particular theory, it is believed that the aforementioned types of emulsions depend on hydrogen bonding, pi stacking, and/or salt bridging of both the dispersed and continuous phases. In this disclosure, the emulsion may be further defined as any one of these four types of emulsions.

As is also known in the art, emulsions may be, to a certain degree, unstable. Typically, there are three types of instability including (i) flocculation, where particles of the dispersed phase form clumps in the continuous phase, (ii) creaming or sedimentation, where the particles of the dispersed phase concentrate respectively towards a top or bottom of the continuous phase, and (iii) breaking and coalescence, where the particles of the dispersed phase coalesce and form a layer of liquid in the continuous phase. The instant emulsion may exhibit one or more of these types of instability. Typically, these types of instability are minimized.

As is also known in the art, emulsions typically have two different types of viscosities, a total viscosity and a viscosity of the dispersed phase. The emulsion of the instant disclosure typically has a total viscosity of at least 10 centistokes at a temperature of 25° C. In various embodiments, the emulsion has a total viscosity of about 10-50,000, 10-30,000, 10-10,000, 10-1,000, 10-500, or 50-200, centistokes at a temperature of 25° C. using a Brookfield rotating disc viscometer equipped with a thermal cell and an SC4-31 spindle operated at a constant temperature of 25° C. and a rotational speed of 5 rpm. The viscosity of the dispersed phase is not limited and is not believed to affect the total viscosity. In one embodiment, the dispersed phase is solid and has an infinite viscosity. All values and ranges of values therebetween the aforementioned values are hereby expressly contemplated in various non-limiting embodiments.

The emulsion may also include a surfactant or more than one surfactant. The surfactants may have the same or different HLBs from each other, as understood in the art and may each independently be a silicone or non-silicone surfactants. In various embodiments, the HLB (hydrophilic-lipophilic balance) of one or more surfactants may be from 5-20, 6-19, 7-18, 8-17, 9-16, 10-15, 11-14, or 12-13. All values and ranges of values therebetween are also expressly contemplated in various non-limiting embodiments.

In various embodiments, one or more of the following surfactants is utilized, wherein the HLB is in parentheses: Genapol UD 050/UD 110 (HLB:11.4/14.4); Brij L4/L23 (HLB: 9.7/16.9); Tergitol 15S5/15S15 (HLB: 10.5/15.4); Tween 20 (HLB:16.7); and/or Lutensol XP-50-140 (HLB: 10-16); or combinations thereof.

In various embodiments, the emulsion includes the (first) surfactant and a second surfactant or multiple surfactants. Surfactants are also known as emulsifiers, emulgents, and tensides. Relative to this disclosure, the terminology "surfactant", "emulsifier", "emulgent", and "tenside" may be used interchangeably. Surfactants reduce a surface tension of a liquid by adsorbing at a liquid-gas interface. Surfactants also reduce interfacial tension between polar and non-polar molecules by adsorbing at a liquid-liquid interface. Without intending to be bound by any particular theory, it is believed that surfactants act at these interfaces and are dependent on various forces including, excluded volume repulsion forces, electrostatic interaction forces, van der Waals forces, entropic forces, and steric forces. In the instant disclosure, the surfactant may be chosen or manipulated based on one or more of these forces.

The surfactant, first and second surfactants, or first/second/and multiple surfactants may independently be chosen from the group of non-ionic surfactants, cationic surfactants, anionic surfactants, amphoteric surfactants, and combinations thereof. Suitable non-ionic surfactants include, but are not limited to, alkylphenol alkoxylates, ethoxylated and propoxylated fatty alcohols, alkyl polyglucosides and hydroxyalkyl polyglucosides, sorbitan derivatives, N-alkylglucamides, alkylene oxide block copolymers, such as block copolymers of ethylene oxide, propylene oxide and/or butylene oxide, polyhydroxy and polyalkoxy fatty acid derivatives, amine oxides, silicone polyethers, various polymeric surfactants based on polysaccharides, polymeric surfactants based on polyvinyl alcohol and polyacrylamide, and combinations thereof.

Suitable cationic surfactants include, but are not limited to, interface-active compounds including ammonium groups, such as alkyldimethylammonium halides and compounds having the chemical formula $RR'R''R'''N^+X^-$ wherein R, R', R", and R''' are independently chosen from the group of alkyl groups, aryl groups, alkylalkoxy groups, arylalkoxy groups, hydroxyalkyl(alkoxy) groups, and hydroxyaryl(alkoxy) groups and wherein X is an anion.

Suitable anionic surfactants include, but are not limited to, fatty alcohol sulfates and sulfates of ethoxylated fatty alcohols. Further non-limiting examples of suitable anionic surfactants include alkanesulfonates, linear alkylbenzenesulfonates, linear alkyltoluenesulfonates, diphenyl sulfonates, and diphenylether sulfonates. Still further, the anionic surfactant may include olefinsulfonates and disulfonates, mixtures of alkene- and hydroxyalkane-sulfonates or di-sulfonates, alkyl ester sulfonates, sulfonated polycarboxylic acids, alkyl glyceryl sulfonates, fatty acid glycerol ester sulfonates, alkylphenol polyglycol ether sulfates, paraffinsulfonates, alkyl phosphates, acyl isothionates, acyl taurates, acyl methyl taurates, alkylsuccinic acids, alkenylsuccinic acids and corresponding esters and amides thereof, alkylsulfosuccinic acids and corresponding amides, mono- and di-esters of sulfosuccinic acids, acyl sarcosinates, sulfated alkyl polyglucosides, alkyl polyglycol carboxylates, hydroxyalkyl sarcosinates, and combinations thereof. Still further, polymeric anionic surfactants based on acrylic acid or sulfonated polystyrene, and combinations thereof, may also be used. Suitable ampholytic surfactants include, but are not limited to, aliphatic derivatives of secondary and/or tertiary amines which include an anionic group, betaine derivatives, and combinations thereof.

Additionally, the surfactant and/or first and second surfactants may independently include aliphatic and/or aromatic alkoxylated alcohols, LAS (linear alkyl benzene sulfonates), paraffin sulfonates, FAS (fatty alcohol sulfates), FAES (fatty alcohol ethersulfates), alkylene glycols, trimethylolpropane ethoxylates, glycerol ethoxylates, pentaerythritol ethoxylates, alkoxylates of bisphenol A, and alkoxylates of 4-methylhexanol and 5-methyl-2-propylheptanol, and combinations thereof. Further, the surfactant and/or first and second surfactants may include alkylpolysaccharides including linear or branched alkyl groups, linear or branched alkenyl groups, alkylphenyl groups, alkylene groups, and/or combinations thereof. Typically, the surfactant is present in an amount of from about 0.1-100, 0.01-5, 0.5-5, or 1.5-2.5, pbw per 100 pbw of the emulsion.

The emulsion may also include a thickener. As is known in the art, thickeners increase a viscosity of the emulsion at low shear rates while maintaining flow properties of the emulsion at higher shear rates. Suitable thickeners for use in the instant disclosure include, but are not limited to, polyalkylene oxides, such as polyethylene oxide, polypropylene oxide, polybutylene oxide, and combinations thereof. In one embodiment, the thickener is chosen from the group of algenic acid and its derivatives, polyethylene oxide, polyvinyl alcohol, methyl cellulose, hydroxypropylmethyl cellulose, alkyl and hydroxyalkyl cellulose, carboxymethyl cellulose, hydroxyethyl cellulose, guar gum, gum arabic, gum ghatic, polyvinylpyrrolidone, starch, modified starch, tamarind gum, xanthan gum, polyacrylamide, polyacrylic acid, and combinations thereof.

The thickener may be combined with the liquid or any other component, before the emulsion is formed. Typically, the thickener is combined with the liquid before the emulsion is formed. In one embodiment, the thickener is combined with a liquid in which it is not soluble and this mixture is combined with the emulsion after it has been formed. Examples of such liquids include, but are not limited to, propylene glycol, ethylene glycol, glycerin, and combinations thereof. The thickener may be present in an amount of from about 0.001-25, 0.05-5, or 0.1-0.5, pbw per 100 pbw of the emulsion.

The emulsion may also include additives. The additives may include, but are not limited to, conductivity-enhancing additives, salts, dyes, perfumes, preservatives, plasticizers, active ingredients, colorants, labeling agents, rust inhibitors, and combinations thereof. In one embodiment, the conductivity-enhancing additive includes an ionic compound. In another embodiment, the conductivity-enhancing additives are generally chosen from the group of amines, organic salts and inorganic salts, and mixtures thereof. Typical conductivity-enhancing additives include amines, quaternary ammonium salts, quaternary phosphonium salts, ternary sulfonium salts, and mixtures of inorganic salts with organic ligands. More typical conductivity-enhancing additives include quaternary ammonium-based organic salts including, but not limited to, tetrabutylammonium chloride, tetrabutylammonium bromide, tetrabutylammonium iodide, phenyltrimethylammonium chloride, phenyltriethylammonium chloride, phenyltrimethylammonium bromide, phenyltrimethylammonium iodide, dodecyltrimethylammonium chloride, dodecyltrimethylammonium bromide, dodecyltrimethylammonium iodide, tetradecyltrimethylammonium chloride, tetradecyltrimethylammonium bromide, tetradecyltrimethylammonium iodide, hexadecyltrimethylammonium chloride, hexadecyltrimethylammonium bromide, and hexadecyltrimethylammonium iodide. The additive may be present in either the continuous or dispersed phase of the emulsion in any amount selected by one of skill in the art. In various embodiments, the amount of the additive is typically of from about 0.0001-25, 0.001-10, or 0.01-1, % based on the total weight of the particles.

In the emulsion, the weight ratio of the continuous phase, e.g. water, the aminosiloxane polymer, and one or more surfactants or other components is not particularly limited.

However, in various embodiments, these three components are present in amounts as set forth below in weight percents (wt. %):

| | | | | | | |
|---|---|---|---|---|---|---|
| Aminosiloxane Polymer (wt. %) | 10-40 | 10-30 | 20-30 | 30-90 | 45-65 | 55-60 |
| One or More Surfactants (wt. %) | 2-25 | 5-20 | 10-15 | 0.5-5 | 1-5 | 2-5 |
| Other Components (wt. %) | 0.05-2 | 0.05-2 | 0.05-2 | 0.05-2 | 0.05-2 | 0.05-2 |
| Continuous Phase | Balance | Balance | Balance | Balance | Balance | Balance |
| Total (pbw) | 100 | 100 | 100 | 100 | 100 | 100 |

This disclosure also provides a method of forming the aminosiloxane polymer. The method includes the steps of providing the polyorganosiloxane having the amino group, providing the alkylamine and/or the alkanolamine, and providing the alkenyl cyclic anhydride. Each of the steps of providing may be further defined as any known in the art. For example, each of the aforementioned components may be provided in a vessel, reactor, etc. and may be provided in a batch-wise or continuous manner and at any appropriate temperature, pressure, rate, and amount, as is understood by those of skill in the art. Each of the polyorganosiloxane having the amino group, the alkylamine, the alkanolamine, and the alkenyl cyclic anhydride may be as described above.

The method also includes the step of reacting the (alkylamine and/or alkanolamine) and the alkenyl cyclic anhydride to form an intermediate, e.g. as described above. More specifically, the alkylamine and the alkenyl cyclic anhydride may react to form the intermediate. Alternatively, the alkanolamine and the alkenyl cyclic anhydride may react to form the intermediate. Even further, both the alkylamine and the alkanolamine may both react with the alkenyl cyclic anhydride to form the intermediate. As described above, one or more major product forms of the intermediate may be formed, as is understood in the art.

When utilized, the alkylamine typically reacts with the alkenyl cyclic anhydride in a mole ratio of from about 10:1, 5:1, or 1:1. Moreover, when utilized, the alkanolamine typically reacts with the alkenyl cyclic anhydride in a mole ratio of from about 10:1, 5:1, or 1:1. Even further, if both the alkylamine and the alkanolamine are utilized, the total amount of the alkylamine and the alkanolamine that are utilized, as a mole ratio to the amount of the alkenyl cyclic anhydride, is typically of from about 10:1, 5:1, or 1:1. All values and ranges of values in between the aforementioned values are hereby expressly contemplated in various non-limiting embodiments. Moreover, this disclosure is not limited to these amounts.

In one embodiment, the step of providing the alkylamine and/or the alkanolamine is further defined as providing the alkylamine in the absence of the alkanolamine. In another embodiment, the step of providing the alkylamine and/or the alkanolamine is further defined as providing the alkanolamine in the absence of the alkylamine. In various embodiments, the alkenyl cyclic anhydride is further defined as maleic anhydride, itaconic anhydride, or combinations thereof.

In other embodiments, the method includes the step of providing a polydialkylsiloxane independently from the alkylamine, the alkanolamine, and/or the alkenyl cyclic anhydride. Alternatively, the polydialkylsiloxane may be provided with the alkylamine, the alkanolamine, and/or the alkenyl cyclic anhydride. The polydialkylsiloxane may act as a diluent in any emulsion described herein and may facilitate or improve film forming ability and/or physical properties of the film when formed on a substrate. In still other embodiments, the polydialkylsiloxane may be added or present in any step of the method or emulsion described herein.

The polydialkylsiloxane may be a single polydialkylsiloxane or a combination of two or more polydialkylsiloxanes. The polydialkylsiloxane is not particularly limited and, in various embodiments, has a weight average molecular weight ($M_w$) of up to 1,000,000 g/mol. In still other embodiments, the polydialkylsiloxane has a $M_w$ of from about 100,000-1,000,000, 100,000-250,000, 100,000-500,000, 100,000-750,000, 250,000-1,000,000, 250,000-750,000, 250,000-500,000, 500,000-750,000, or 750,000-1,000,000, g/mol. A mixture of a polydialkylsiloxane having a Mw of up to 1,000,000 g/mol and aminosiloxane polymer may also be utilized in this disclosure, e.g. in the emulsion or the method, wherein a ratio of the polydialkylsiloxane to the aminosiloxane polymer is from about 0.1-100. All values and ranges of values between the aforementioned values are hereby expressly contemplated in various non-limiting embodiments.

In various embodiments, the polydialkylsiloxane has the general formula:

wherein $R^a$ is an alkyl group having 1-30 carbon atoms, $R^b$ may be an $R^a$ alkyl group or a hydroxy group, and the subscript "x" represents the Dp and is >1,000. In various embodiments, the polydialkylsiloxane is a trimethylsiloxy terminated polydimethylsiloxane fluid having a Dp (x) that is sufficient to provide a polydimethylsiloxane fluid viscosity of ≥50,000 mm/s (or 50,000 centistokes, abbreviated as cS) at 23° C. Alternatively, (x) is sufficient to provide a polydimethylsiloxane fluid viscosity of ≥100,000 mm/s at 23° C. Alternatively, (x) is sufficient to provide a polydimethylsiloxane fluid viscosity of ≥500,000 mm/s at 23° C. Non-limiting commercial products of trimethylsiloxy terminated polydimethylsiloxane fluids suitable for use herein as the polydialkylsiloxane include Dow Corning 200® fluids having a viscosity of ≥50,000 cS. All values and ranges of values between the aforementioned values are hereby expressly contemplated in various non-limiting embodiments.

The intermediate is not particularly limited and may be the reaction product of any alkylamine and alkenyl cyclic anhydride, any alkanolamine and alkenyl cyclic anhydride, or any alkylamine and alkanolamine and alkenyl cyclic anhydride. Typically, a secondary nitrogen atom of an amine group (e.g. NH) reacts with the alkenyl cyclic anhydride to form the intermediate. However, this disclosure is not limited to this mechanism.

In various examples, the aforementioned reaction(s), utilizing maleic anhydride and itaconic anhydride as non-limiting examples of the alkenyl cyclic anhydride, may proceed as follows:

Reaction Scheme One
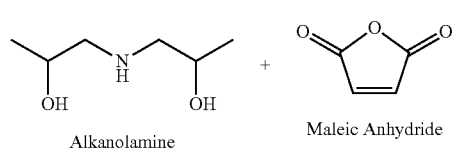
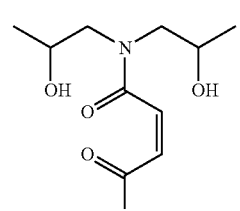
Intermediate
Reaction Scheme Two
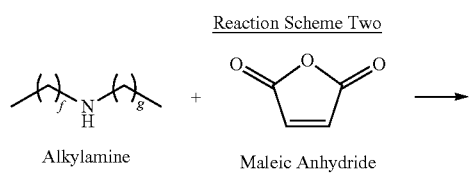
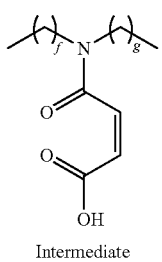
Intermediate
wherein f and g are each independently any integer, so long as f+g is ≥1.
Reaction Scheme Three
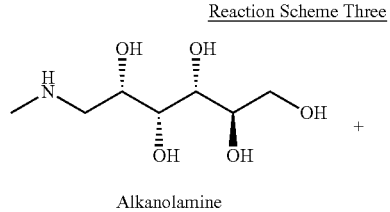
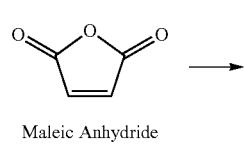
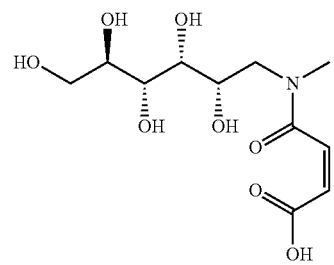
Intermediate
Reaction Scheme Four
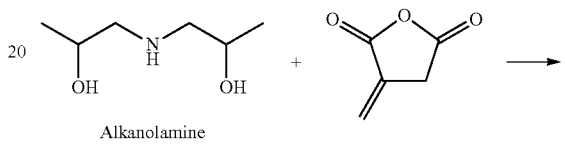
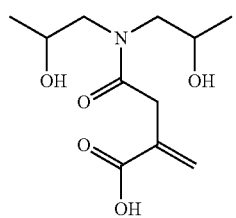
Intermediate
Reaction Scheme Five
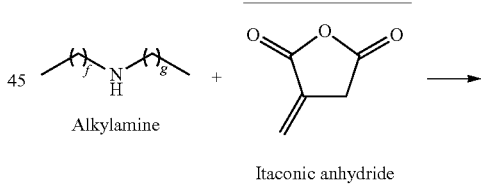
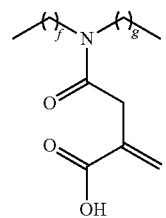
Intermediate
wherein f and g are each independently any integer, so long as f+g is ≥1.

Reaction Scheme Six

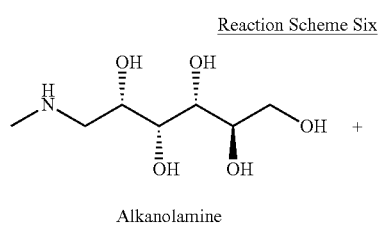

Alkanolamine

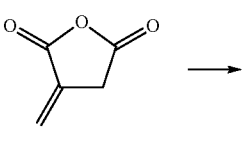

Itaconic anhydride

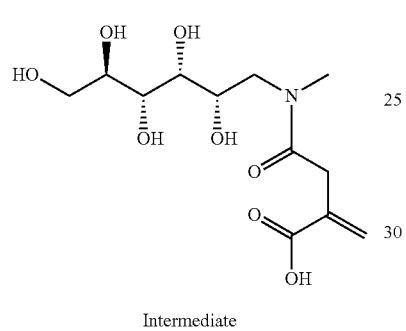

Intermediate

Reaction Scheme Seven

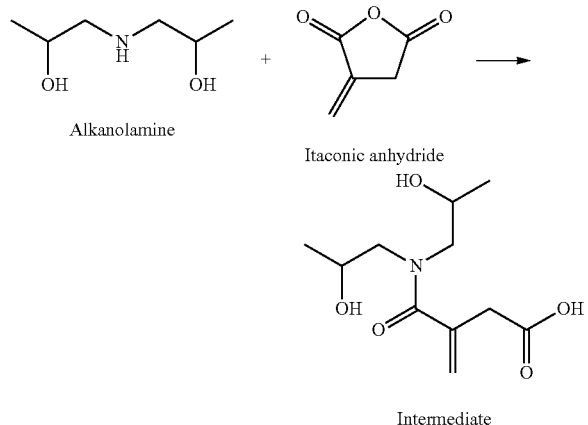

Intermediate

Reaction Scheme Eight

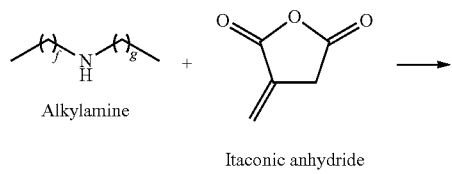

Alkylamine   Itaconic anhydride

-continued

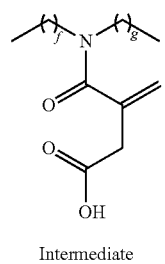

Intermediate wherein f and g are each independently any integer, so long as f+g is ≥1.

Reaction Scheme Nine

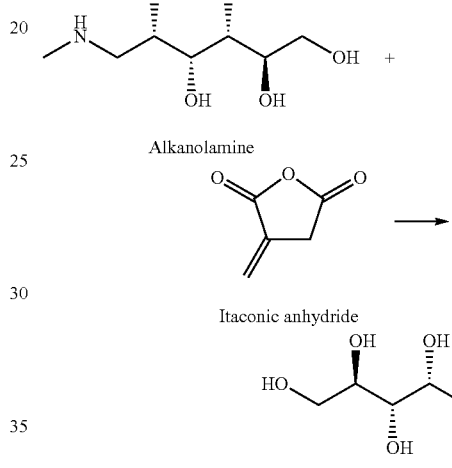

Alkanolamine

Itaconic anhydride

Intermediate

In each of the aforementioned reaction schemes one through nine, where a cis- or trans-isomer/moiety is illustrated, the other isomer/moiety is also contemplated (not shown). Moreover, where an acidic or basic component is illustrated, it may also be coordinated, i.e., in a salt form (not shown) that is contemplated for purposes of this disclosure. For example, acidic groups may be coordinated with a surrounding amine to form an acid-based ionic salt.

The method also includes the step of reacting the intermediate and the polyorganosiloxane having the amino group to form the aminosiloxane polymer. The polyorganosiloxane typically reacts with the intermediate in a mole ratio of from about 3.5:1, 3:1, 2.5:1, or 2:1. All values and ranges of values therebetween are also hereby expressly contemplated in various non-limiting embodiments. However, this disclosure is not limited to these amounts.

The intermediate is not particularly limited. Accordingly, this method step is not particularly limited relative to the intermediate or the polyorganosiloxane, so long as the aminosiloxane polymer is formed, as described above. Typically, the amino group of the polyorganosiloxane reacts with a (cis) double bond of the intermediate (e.g. if formed using maleic anhydride). In various non-limiting examples, the aforementioned reaction(s) may proceed as follows wherein the varying symmetric chemical structures (based on maleic anhydride) and asymmetric structures (based on itaconic anhydride) are shown below:

Reaction Scheme Ten

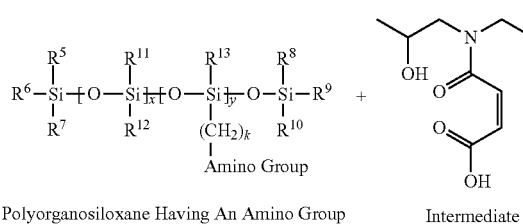

Polyorganosiloxane Having An Amino Group    Intermediate

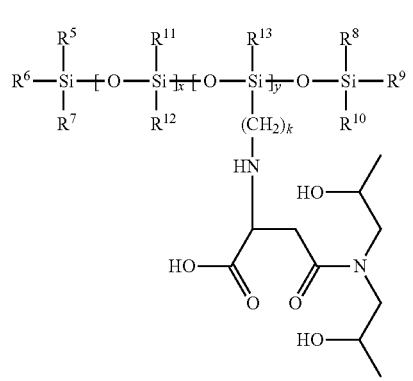

Aminosiloxane Polymer wherein k is ≥0.

Reaction Scheme Eleven

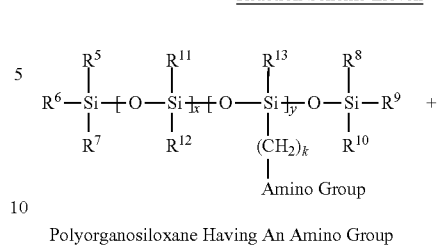 + 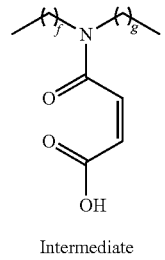

Polyorganosiloxane Having An Amino Group    Intermediate

↓

Aminosiloxane Polymer wherein k is ≥0 and f and g are each independently any integer, so long as f+g is ≥1.

Reaction Scheme Twelve

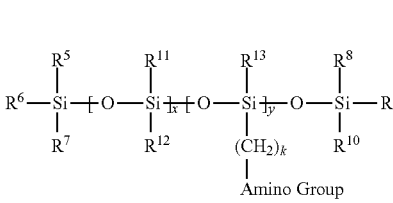 + 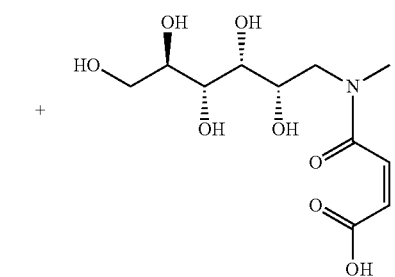

Polyorganosiloxane Having An Amino Group

Intermediate

19
-continued
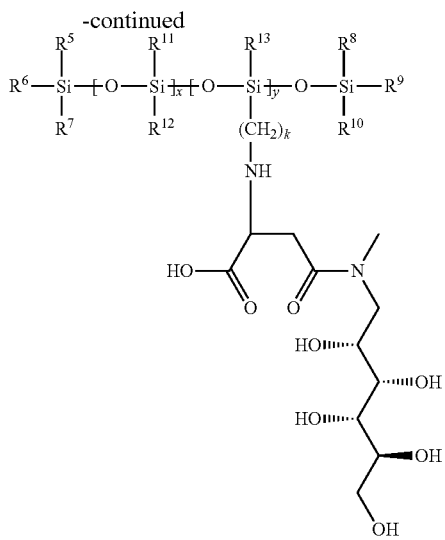
Aminosiloxane Polymer
wherein k is ≥0.
Reaction Scheme Thirteen
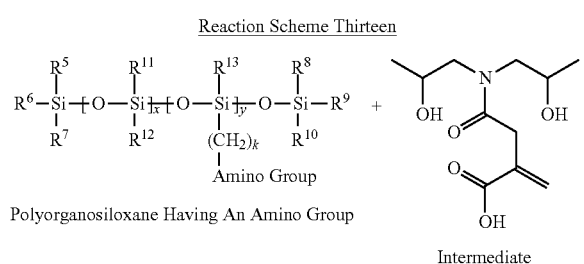
Polyorganosiloxane Having An Amino Group    Intermediate
↓
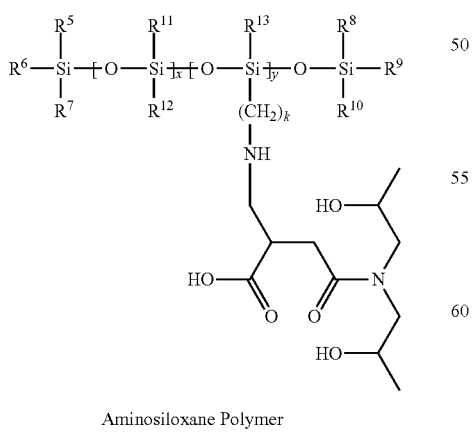
Aminosiloxane Polymer
wherein k is ≥0.
20
Reaction Scheme Fourteen
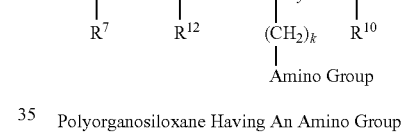
Polyorganosiloxane Having An Amino Group    Intermediate
↓
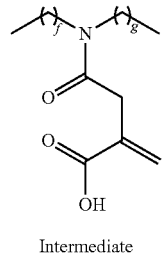
Aminosiloxane Polymer
wherein k is ≥0 and f and g are each independently any integer, so long as f+g is ≥1.

Reaction Scheme Fifteen
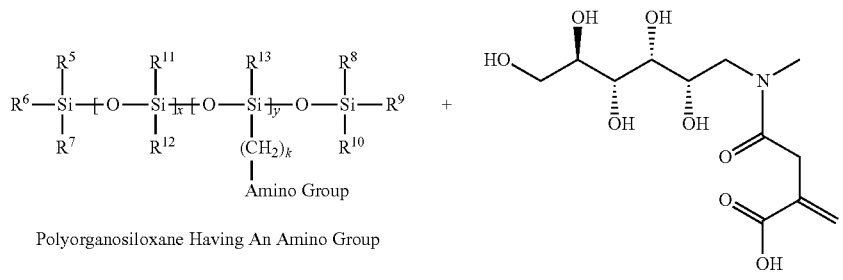
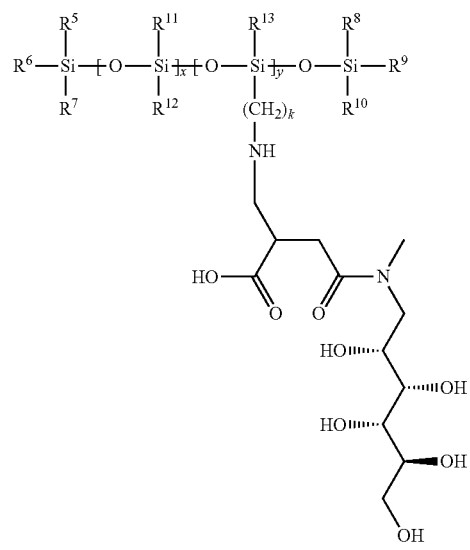
Aminosiloxane Polymer
wherein k is ≥0.
Reaction Scheme Sixteen
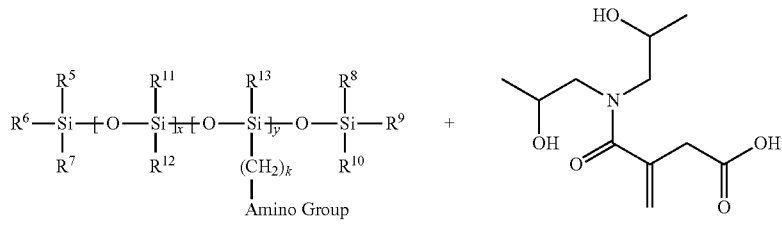

-continued
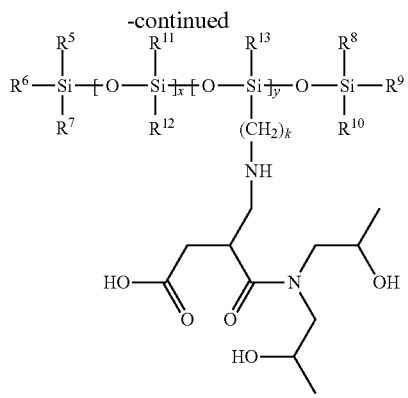
Aminosiloxane Polymer
wherein k is ≥0.
Reaction Scheme Seventeen
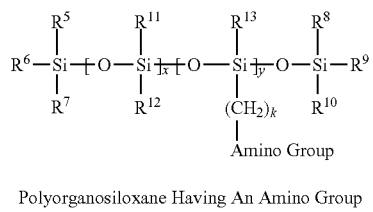 + 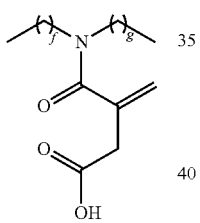
Polyorganosiloxane Having An Amino Group
Intermediate
↓
-continued
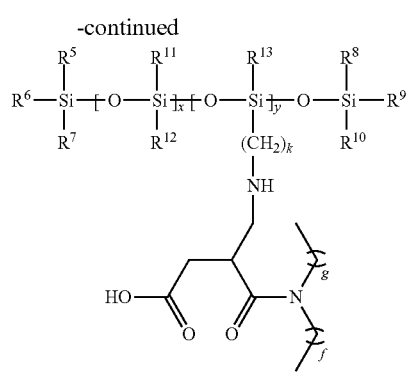
Aminosiloxane Polymer
wherein k is ≥0 and f and g are each independently any integer, so long as f+g≥1.
Reaction Scheme Eighteen
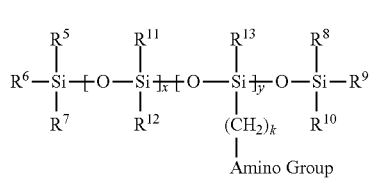 + 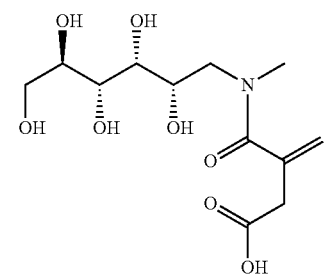
Polyorganosiloxane Having An Amino Group
Intermediate

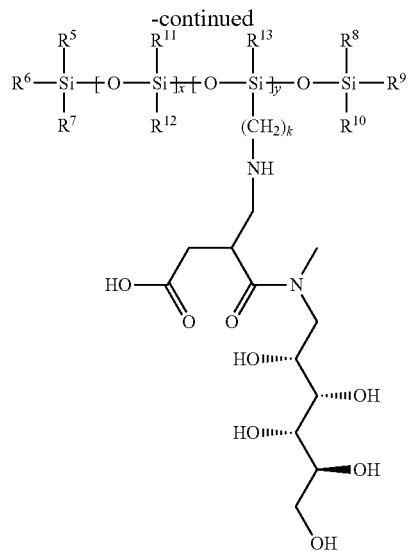

Aminosiloxane Polymer wherein k is ≥0.

In each of the aforementioned reaction schemes ten through eighteen, the "amino group" of the polyorganosiloxane is first generalized in words and then generically shown as (NH). However, NH is chosen merely for illustrative purposes and does not limit this disclosure. Moreover, in each of these reaction schemes, each of $R^5$-$R^{13}$, "x" and "y" are independently as described above. Further, where a cis- or trans-isomer/moiety is illustrated, the other isomer/moiety is also contemplated (not shown). Where an acidic or basic component is illustrated, it may also be coordinated, i.e., in a salt form (not shown) that is contemplated for purposes of this disclosure. For example, acidic groups may be coordinated with a surrounding amine to form an acid-based ionic salt.

In one embodiment, the step of providing the polyorganosiloxane having the amino group is further defined as providing a first emulsion including a first continuous phase and a first dispersed phase including the polyorganosiloxane having the amino group. The first continuous phase may be any type of continuous phase described above. Moreover, the first emulsion may be any type of emulsion described above.

The step of reacting the intermediate and the polyorganosiloxane having the amino group may be further defined as adding the intermediate to the first emulsion to form a second emulsion. Typically, the second emulsion includes a second continuous phase and a second dispersed phase. Upon formation of the second emulsion, the second dispersed phase typically includes or is the intermediate and the polyorganosiloxane having the amino group. After in-situ reaction of these two components, the second dispersed phase then typically includes or is the aminosiloxane polymer. The second continuous phase may be any type of continuous phase described above. Moreover, the second emulsion may be any type of emulsion described above.

The method may also include heating the first and/or second emulsions at or to a temperature of about 10-90, 20-90, 20-80, 25-75, 30-70, 35-65, 40-60, 45-55, or 50-55, ° C., to form the aminosiloxane polymer in-situ in the second emulsion. The terminology "in-situ" describes an embodiment wherein the aminosiloxane polymer is formed in the emulsion, e.g. in the second dispersed phase of the second emulsion. However, it is contemplated that the aminosiloxane polymer may be formed apart from an emulsion and later emulsified using any technique known in the art.

In various embodiments, the polyorganosiloxane having the amino group is present in the first dispersed phase of the first emulsion in an amount of from about 10-90, 10-80, 10-70, 15-65, 20-60, 25-55, 30-50, 35-45, or 40-45, pbw per 100 pbw of the first emulsion. In other embodiments, the polyorganosiloxane having the amino group is present in the second dispersed phase of the second emulsion in an amount of from about 10-70, 15-65, 20-60, 25-55, 30-50, 35-45, or 40-45, pbw per 100 pbw of the second emulsion. In still other embodiments, the intermediate is present in the second dispersed phase of the second emulsion in an amount of from about 0.1-30, 0.1-1, 0.1-0.9, 0.2-0.8, 0.3-0.7, 0.4-0.6, 0.5-0.6, alternatively 1-30, 1-5, 1-10, 5-20, 10-25, or 15-20, pbw per 100 pbw of the second emulsion. In addition, after formation (e.g. in-situ formation in the second dispersed phase of the second emulsion), the aminosiloxane polymer may be present in the second emulsion in amount of from about 10-90, 10-80, 10-70, 15-65, 20-60, 25-55, 30-50, 35-45, or 40-45, pbw per 100 pbw of the second emulsion. The amount of the aminosiloxane polymer in the second emulsion may be as described above. All values and ranges of values between and including the aforementioned values, along with all combinations of the above, are hereby expressly contemplated in various non-limiting embodiments.

Any of the aforementioned emulsions may be formed by any suitable means known in the art and typically includes combining a liquid continuous phase with an immiscible dispersed phase. The liquid continuous phase may be any described above. The step of forming the emulsion may include emulsifying any one or more of the aforementioned compounds. A surfactant and/or thickener may be added to the liquid continuous phase prior to, concurrent with, or after combination with the aminosiloxane polymer and/or particles.

In various embodiments, one or more of the aforementioned emulsion is formed by simple agitation to form a coarse mixture, e.g. a water in polymer mixture. This mixture may then be emulsified. During emulsification, the coarse mixture can be inverted into an emulsion. The emulsification can be accomplished by conventional methods, such as with ribbon mixers, plow mixers, fluidizing paddle mixers, sigma blade mixers, tumble blenders, vortex mixers, feed mixers, vertical mixers, horizontal mixers, and combinations thereof.

In various additional embodiments, this disclosure provides a film formed from the emulsion and/or including or being the aminosiloxane polymer. In other embodiments, this disclosure provides a use of the aminosiloxane polymer, the emulsion, or the film as a cosmetic ingredient. Alternatively, this disclosure provides a use of the aminosiloxane polymer, the emulsion, or the film as a fabric treating agent. Alternatively, this disclosure provides a use of the aminosiloxane polymer, the emulsion, or the film as a fiber treating agent or composition. Still further, this disclosure provides a cosmetic composition including the aminosiloxane polymer, the emulsion, or the film. This disclosure also provides a hair care composition including the aminosiloxane polymer, the emulsion, or the film. This disclosure further provides a fabric treating composition including the aminosiloxane polymer, the emulsion, or the film. This disclosure further provides a fiber treating composition including the aminosiloxane polymer, the emulsion, or the film.

Referring now to the film, the film may be of any dimensions relative to length, width, and thickness. Typically, the film is formed using the aminosiloxane polymer and/or the emulsion. For example, the aminosiloxane polymer and/or the emulsion may be poured onto a substrate and then dried to form the film. The substrate may be any in the art including plastic, wood, glass, polymers, metal, human skin, human hair, fabric, textiles, and the like.

The emulsion, film, and/or aminosiloxane polymer of the instant disclosure can be useful in many applications, for example in personal care applications, such as on hair, skin, mucous membrane or teeth. In many of these applications, the emulsion, film, and/or aminosiloxane polymer is lubricious and improves properties of skin creams, skin care lotions, moisturizers, facial treatments, such as acne or wrinkle removers, personal and facial cleansers, bath oils, perfumes, fragrances, colognes, sachets, sunscreens, pre-shave and after shave lotions, shaving soaps and shaving lathers. The emulsion, film, and/or aminosiloxane polymer can likewise be used in hair shampoos, hair conditioners, hair sprays, mousses, permanents, depilatories, and cuticle coats, for example to provide styling and conditioning benefits. In cosmetics, the emulsion, film, and/or aminosiloxane polymer may function as a leveling and spreading agent for pigment in make-ups, color cosmetics, foundations, blushes, lipsticks, eye liners, mascaras, oil removers, color cosmetic removers and powders. The emulsion, film, and/or aminosiloxane polymer may also be useful as a delivery system for oil and water soluble substances, such as vitamins, organic sunscreens, ceramides, pharmaceuticals and the like. When compounded into sticks, gels, lotions aerosols and roll-ons, the emulsion, film, and/or aminosiloxane polymer may impart a dry silky-smooth payout. The emulsion, film, and/or aminosiloxane polymer may also be mixed with deposition polymers, surfactants, detergents, antibacterials, anti-dandruffs, foam boosters, proteins, moisturizing agents, suspending agents, opacifiers, perfumes, coloring agents, plant extracts, polymers, and other conventional care ingredients. In one embodiment, the emulsion, film, and/or aminosiloxane polymer is included in a water based composition that is chosen from the group of cosmetic compositions, fabric treating compositions, fiber treating compositions, hair care compositions, fiber care compositions, and combinations thereof. The emulsion, film, and/or aminosiloxane polymer may be used in personal care products in amounts of from about 0.01-50, or 0.1-25, wt. % of a personal care product.

The emulsion, film, and/or aminosiloxane polymer may also be useful for numerous other applications, such as textile fiber treatment, leather lubrication, fabric softening, release agents, water based coatings, oil drag reduction, particularly in crude oil pipelines, lubrication, facilitation of cutting cellulose materials, and in many other areas where silicones are conventionally used. The emulsion, film, and/or aminosiloxane polymer may also be used to reduce oil drag. The emulsion, film, and/or aminosiloxane polymer can also be used in antimicrobial applications, in preservatives, deodorants, wound dressings, and dentifrices, and as a catalyst in organic synthesis reactions. Further, the emulsion, film, and/or aminosiloxane polymer can be used in filters and solar cells. The emulsion also allows the particles of the aminosiloxane polymer to be handled easily and allows for quality checks on the particles to be performed efficiently and accurately. The emulsion also allows for a variety of types of compounds to be utilized to form particles that can be customized based on desired physical and chemical properties. The emulsion can also be effectively utilized in a variety of industries including in cosmetic and coating applications.

This disclosure also provides a personal care composition, which may also be described as a personal care product composition. The personal care composition includes the aminosiloxane polymer. The personal care composition may be in the form of a cream, a gel, a powder, a paste, or a freely pourable liquid. Generally, such compositions can be prepared at room temperature if no solid materials at room temperature are present in the compositions, using simple propeller mixers, Brookfield counter-rotating mixers, or homogenizing mixers. No special equipment or processing conditions are typically required. Depending on the type of form made, the method of preparation will be different, but such methods are well known in the art.

The personal care composition may be functional with respect to the portion of the body to which it is applied, cosmetic, therapeutic, or some combination thereof. Conventional examples of such products include, but are not limited to, antiperspirants and deodorants, skin care creams, skin care lotions, moisturizers, facial treatments, such as acne or wrinkle removers, personal and facial cleansers, bath oils, perfumes, colognes, sachets, sunscreens, pre-shave and after-shave lotions, shaving soaps, and shaving lathers, hair shampoos, hair conditioners, hair colorants, hair relaxants, hair sprays, mousses, gels, permanents, depilatories, and cuticle coats, make-ups, color cosmetics, foundations, concealers, blushes, lipsticks, eyeliners, mascara, oil removers, color cosmetic removers, and powders, medicament creams, pastes or sprays including anti-acne, dental hygienic, antibiotic, healing promotive, nutritive and the like, which may be preventative and/or therapeutic. In general, the personal care composition may be formulated with a carrier that permits application in any conventional form, including but not limited to liquids, rinses, lotions, creams, pastes, gels, foams, mousses, ointments, sprays, aerosols, soaps, sticks, soft solids, solid gels, and gels. Suitable carriers are appreciated in the art.

The personal care composition can be used in or for a variety of personal, household, and healthcare applications. In particular, the aminosiloxane polymer and/or personal care compositions of the present disclosure may be used in the personal care products as described in U.S. Pat. Nos. 6,051,216, 5,919,441, 5,981,680; WO 2004/060271 and WO 2004/060101; in sunscreen compositions as described in WO 2004/060276; in cosmetic compositions also containing film-forming resins, as described in WO 03/105801; in the cosmetic compositions as described in US Pat. App. Pub. Nos. 2003/0235553, 2003/0072730 and 2003/0170188, in EP Pat. Nos. 1,266,647, 1,266,648, and 1,266,653, in WO 03/105789, WO 2004/000247 and WO 03/106614; as additional agents to those described in WO 2004/054523; in long wearing cosmetic compositions as described in US Pat. App. Pub. No. 2004/0180032; and/or in transparent or translucent care and/or make up compositions as described in WO 2004/054524, all of which are expressly incorporated herein by reference in various non-limiting embodiments.

The personal care composition and/or aminosiloxane polymer can be used by the standard methods, such as applying them to the human body, e.g. skin or hair, using applicators, brushes, applying by hand, pouring them and/or possibly rubbing or massaging the composition onto or into the body. Removal methods, for example for color cosmetics are also well known standard methods, including washing, wiping, peeling and the like. For use on the skin, the personal care composition and/or aminosiloxane polymer may be used in a conventional manner for example for conditioning the skin. An effective amount of the personal care composition and/or aminosiloxane polymer may be applied to the skin. Such effective amounts generally are from about 1-3 mg/cm$^2$. Application to the skin typically includes working the personal care composition and/or aminosiloxane polymer into the skin. This method for applying to the skin typically includes the steps of contacting the skin with the personal care composition and/or aminosiloxane polymer in an effective amount and then rubbing the personal care composition and/or aminosiloxane polymer into the skin. These steps can be repeated as many times as desired to achieve the desired benefit.

Use of the personal care composition and/or aminosiloxane polymer on hair may use a conventional manner for conditioning hair. An effective amount of the personal care composition and/or aminosiloxane polymer for conditioning hair is applied to the hair. Such effective amounts generally are from about 1-50, or 1-20, g. Application to the hair typically includes working the personal care composition and/or aminosiloxane polymer through the hair such that most or all of the hair is contacted with the personal care composition and/or aminosiloxane polymer. This method for conditioning the hair typically includes the steps of applying an effective amount of the personal care composition and/or aminosiloxane polymer to the hair, and then working the personal care composition and/or aminosiloxane polymer through the hair. These steps can be repeated as many times as desired to achieve the desired conditioning benefit.

Non-limiting examples of additives which may be formulated into the personal care composition, cosmetic composition, fabric treating composition, hair care composition, emulsion, film, and/or aminosiloxane polymer, or any other compositions described above, include, but are not limited to, additional silicones, anti-oxidants, cleansing agents, colorants, additional conditioning agents, deposition agents, electrolytes, emollients and oils, exfoliating agents, foam boosting agents, fragrances, humectants, occlusive agents, pediculicides, pH control agents, pigments, preservatives, biocides, other solvents, stabilizers, sun-screening agents, suspending agents, tanning agents, other surfactants, thickeners, vitamins, botanicals, waxes, rheology-modifying agents, anti-dandruff, anti-acne, anti-cane and wound healing-promotion agents.

The personal care composition, such as a shampoo or cleanser, emulsion, film, aminosiloxane polymer, and/or any other composition described above, may include at least one anionic detersive surfactant. This can be any of the well-known anionic detersive surfactants typically used in shampoo formulations. These anionic detersive surfactants can function as cleansing agents and foaming agents in the shampoo compositions. The anionic detersive surfactants are exemplified by alkali metal sulforicinates, sulfonated glyceryl esters of fatty acids, such as sulfonated monoglycerides of coconut oil acids, salts of sulfonated monovalent alcohol esters, such as sodium oleylisethianate, amides of amino sulfonic acids, such as the sodium salt of oleyl methyl tauride, sulfonated products of fatty acids nitriles, such as palmitonitrile sulfonate, sulfonated aromatic hydrocarbons, such as sodium alpha-naphthalene monosulfonate, condensation products of naphthalene sulfonic acids with formaldehyde, sodium octahydroanthracene sulfonate, alkali metal alkyl sulfates, such as sodium lauryl sulfate, ammonium lauryl sulfate or triethanol amine lauryl sulfate, ether sulfates having alkyl groups of 8 or more carbon atoms, such as sodium lauryl ether sulfate, ammonium lauryl ether sulfate, sodium alkyl aryl ether sulfates, and ammonium alkyl aryl ether sulfates, alkylarylsulfonates having 1 or more alkyl groups of 8 or more carbon atoms, alkylbenzenesulfonic acid alkali metal salts exemplified by hexylbenzenesulfonic acid sodium salt, octylbenzenesulfonic acid sodium salt, decylbenzenesulfonic acid sodium salt, dodecylbenzenesulfonic acid sodium salt, cetylbenzenesulfonic acid sodium salt, and myristylbenzenesulfonic acid sodium salt, sulfuric esters of polyoxyethylene alkyl ether including $CH_3(CH_2)_6 CH_2O(C_2H_4O)_2SO_3H$, $CH_3(CH_2)_7CH_2O(C_2H_4O)_{3.5}SO_3H$, $CH_3(CH_2)_8CH_2O(C_2H_4O)_8SO_3H$, $CH_3(CH_2)_{19}CH_2O(C_2H_4O)_4SO_3H$, and $CH_3(CH_2)_{10}CH_2O(C_2H_4O)_6SO_3H$, sodium salts, potassium salts, and amine salts of alkylnaphthylsulfonic acid. Typically, the detersive surfactant is chosen from sodium lauryl sulfate, ammonium lauryl sulfate, triethanolamine lauryl sulfate, sodium lauryl ether sulfate, and ammonium lauryl ether sulfate. The anionic detersive surfactant can be present in the shampoo composition in an amount from about 5-50, or 5-25, wt. % based on the total weight of the shampoo composition.

The personal care composition, emulsion, film, aminosiloxane polymer, and/or any other composition described above, may include at least one cationic deposition aid, typically a cationic deposition polymer. The cationic deposition aid is typically present at levels of from about 0.001-5, 0.01-1, or 0.02-0.5, % by weight. The cationic deposition polymer may be a homopolymer or be formed from two or more types of monomers. The molecular weight of the cationic deposition polymer is typically from about 5,000-10,000,000, 10,000, or 100,000-2,000,000. The cationic deposition polymers typically have cationic nitrogen containing groups, such as quaternary ammonium or protonated amino groups, or a combination thereof. The cationic charge density should be ≥0.1 meq/g, typically >0.8 or higher. The cationic charge density should not exceed 4 meq/g, it is typically <3 and more typically <2 meq/g. The charge density can be measured using the Kjeldahl method and is within the above limits at the desired pH of use, which will in general be from about 3-9 or 4-8. It is contemplated that any and all values or ranges of values between those described above may also be utilized. The cationic nitrogen-containing group is typically present as a substituent on a fraction of the total monomer units of the cationic deposition polymer. Thus when the cationic deposition polymer is not a homopolymer it can include spacer noncationic monomer units. Such cationic deposition polymers are described in the CTFA Cosmetic Ingredient Directory, 3rd edition, which is expressly incorporated herein by reference in one or more non-limiting embodiments. Suitable cationic deposition aids include, for example, copolymers of vinyl monomers having cationic amine or quaternary ammonium functionalities with water soluble spacer monomers, such as (meth)acrylamide, alkyl and dialkyl (meth)acrylamides, alkyl (meth)acrylate, vinyl caprolactone and vinyl pyrrolidine. The alkyl and dialkyl substituted monomers typically have $C_1$-$C_7$ alkyl groups, more typically $C_1$-$C_3$ alkyl groups. Other suitable spacers include vinyl esters, vinyl alcohol, maleic anhydride, propylene glycol and ethylene glycol. The cationic amines can be primary, secondary or tertiary amines, depending upon the particular species and the pH of the composition. In general secondary and tertiary amines, especially tertiary, are typical. Amine substituted vinyl monomers and amines can be polymerized in the amine form and then converted to ammonium by quaternization. Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings, such as pyridinium, imidazolium, and quaternized pyrrolidine, e.g. alkyl vinyl imidazolium, and quaternized pyrrolidine, e.g. alkyl vinyl imidazolium, alkyl vinyl pyridinium, alkyl vinyl pyrrolidine salts. The alkyl portions of these monomers are typically lower alkyls, such as the $C_1$-$C_7$ alkyls, more typically $C_1$ and $C_2$ alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are typically $C_1$-$C_7$ hydrocarbyls, more typically $C_1$-$C_3$ alkyls. The cationic deposition aids can include combinations of monomer units derived from amine- and/or quaternary ammonium-substituted monomer and/or compatible spacer monomers. Suitable cationic deposition aids include, for example: copolymers of 1-vinyl-2-pyrrolidine and 1-vinyl-3-methylimidazolium salt (e.g. Chloride salt) (referred to in the industry by the Cosmetic, Toiletry, and Fragrance Association, "CTFA" as Polyquaternium-16), such as those commercially available from BASF Wyandotte Corp. (Parsippany, N.J., USA) under the LUVIQUAT trade name (e.g. LUVIQUAT FC 370); copolymers of 1-vinyl-2-pyrrolidine and dimethylaminoethyl methacrylate (referred to in the industry by CTFA as Polyquaternium-11), such as those commercially from Gar Corporation (Wayne, N.J., USA) under the GAFQUAT trade name (e.g. GAFQUAT 755N); cationic diallyl quaternary ammonium-containing polymer including, for example, dimethyl diallylammonium chloride homopolymer and copolymers of acrylamide and dimethyl diallylammonium chloride, referred to in the industry (CTFA) as Polyquaternium 6 and Polyquaternium 7, respectively; mineral acid salts of aminoalkyl esters of homo- and copolymers of unsaturated carboxylic acids having from 3-5 carbon atoms, as described in U.S. Pat. No. 4,009,256; and cationic polyacrylamides as described in UK Application No. 9403156.4 (WO95/22311), each of which is expressly incorporated herein in one or more non-limiting embodiments. Other cationic deposition aids that can be used include polysaccharide polymers, such as cationic cellulose derivatives and cationic starch derivatives. Cationic polysaccharide polymer materials suitable for use in compositions of the disclosure include those of the formula: A-O (R—N+R1R2R3X—) wherein: A is an anhydroglucose residual group, such as starch or cellulose anhydroglucose residual, R is an alkylene oxyalklene, polyoxyalkylene, or hydroxyalkylene group, or combination thereof, R1, R2 and R3 independently are alkyl, aryl, alkylaryl, arylalkyl, alkoxyalkyl, or alkoxyaryl groups, each group containing up to 18 carbon atoms, and the total number of carbon atoms for each cationic moiety (i.e., the sum of carbon atoms in R1, R2, R3) typically being 20 or less, and X is an anionic counterion. Cationic cellulose is available from Amerchol Corp. (Edison, N.J., USA) in their Polymer iR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the trade name Polymer LM-200. Other cationic deposition aids that can be used include cationic guar gum derivatives, such as guar hydroxypropyltrimonium chloride (Commercially available from Celanese Corp. in their Jaguar trademark series). Other materials include quaternary nitrogen-containing cellulose ethers (e.g. as described in U.S. Pat. No. 3,962,418), and copolymers of etherified cellulose and starch (e.g. as described in U.S. Pat. No. 3,958,581), each of which is expressly incorporated herein by reference in one or more non-limiting embodiments.

The personal care composition, emulsion, film, aminosiloxane polymer, and/or any other composition described above, may include a foam boosting agent. A foam boosting agent is an agent which increases the amount of foam available from a system at a constant molar concentration of surfactant, in contrast to a foam stabilizer which delays the collapse of a foam. Foam building is provided by adding to the aqueous media, a foam boosting effective amount of a foam boosting agent. The foam boosting agent is typically chosen from fatty acid alkanolamides and amine oxides. The fatty acid alkanolamides are exemplified by isostearic acid diethanolamide, lauric acid diethanolamide, capric acid diethanolamide, coconut fatty acid diethanolamide, linoleic acid diethanolamide, myristic acid diethanolamide, oleic acid diethanolamide, stearic acid diethanolamide, coconut fatty acid monoethanolamide, oleic acid monoisopropanolamide, and lauric acid monoisopropanolamide. The amine oxides are exemplified by N-cocodimethylamine oxide, N-lauryl dimethylamine oxide, N-myristyl dimethylamine oxide, N-stearyl dimethylamine oxide, N-cocamidopropyl dimethylamine oxide, N-tallowamidopropyl dimethylamine oxide, bis(2-hydroxyethyl) $C_{12-15}$ alkoxypropylamine oxide. Typically a foam boosting agent is chosen from lauric acid diethanolamide, N-lauryl dimethylamine oxide, coconut acid diethanolamide, myristic acid diethanolamide, and oleic acid diethanolamide. The foam boosting agent is typically present in the shampoo compositions in an amount from about 1-15, or 2-10, wt. % based on the total weight of the composition. The composition may further include a polyalkylene glycol to improve lather performance. Concentration of the polyalkylene glycol in the shampoo composition may be from about 0.01-5, 0.05-3, or 0.1-2, % by weight of the shampoo composition. The optional polyalkylene glycols are characterized by the general formula: $H(OCH_2CHR)_n$—OH wherein R is chosen from H, methyl, and combinations thereof. When R is H, these materials are polymers of ethylene oxide, which are also known as polyethylene oxides, polyoxyethylenes, and polyethylene glycols. When R is methyl, these materials are polymers of propylene oxide, which are also known as polypropylene oxides, polyoxypropylenes, and polypropylene glycols. When R is methyl, it is also understood that various positional isomers of the resulting polymers can exist. In the above structure, "n" has an average value of from 1,500-25,000, 2,500-20,000, or 3,500-15,000. Polyethylene glycol polymers useful herein are PEG-2M wherein R equals H and "n" has an average value of 2,000 (PEG-2M is also known as Polyox WSR9N-10, which is available from Union Carbide and as PEG-2,000); PEG-5M wherein R equals H and "n" has an average value of 5,000 (PEG-5M is also known as Polyox WSRO N-35 and Polyox WSRS N-80, both available from Union Carbide and as PEG-5,000 and Polyethylene Glycol 300,000); PEG-7M wherein R equals H and "n" has an average value of 7,000 (PEG-7M is also known as Polyox WSRO N-750 available from Union Carbide); PEG-9M wherein R equals H and "n" has an average value of 9,000 (PEG 9-M is also known as Polyox WSRS N-3333 available from Union Carbide); and PEG-14 M wherein R equals H and "n" has an average value of 14,000 (PEG-14M is also known as Polyox WSRO N-3000 available from Union Carbide). Other useful polymers include the polypropylene glycols and mixed polyethylene/polypropylene glycols.

The personal care composition, emulsion, film, aminosiloxane polymer, and/or any other composition described above, include a suspending agent at concentrations effective for suspending a silicone conditioning agent, or other water-insoluble material, in dispersed form in the personal care composition. Such concentrations may be from about 0.1-10%, or 0.3-5.0%, by weight of the personal care composition. Suspending agents include crystalline suspending agents which can be categorized as acyl derivatives, long chain amine oxides, and combinations thereof, concentrations of which can be from about 0.1-5.0%, or 0.5-3.0%, by weight of the shampoo compositions. These suspending agents are described in U.S. Pat. No. 4,741,855, which is expressly incorporated herein by reference in one or more non-limiting embodiments. These typical suspending agents include ethylene glycol esters of fatty acids typically having from 16-22 carbon atoms. More typical are the ethylene glycol stearates, both mono and distearate, but particularly the distearate containing <7% of the mono stearate. Other suitable suspending agents include alkanol amides of fatty acids, typically having from 16-22 carbon atoms, more typically 16-18 carbon atoms, typical examples of which include stearic monoethanolamide, stearic diethanolamide, stearic monoisopropanolamide and stearic monoethanolamide stearate. Other long chain acyl derivatives include long chain esters of long chain fatty acids (e.g. stearyl stearate, cetyl palmitate, etc.); glyceryl esters (e.g. glyceryl distearate) and long chain esters of long chain alkanol amides (e.g. stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the typical materials listed above may be used as suspending agents. For example, it is contemplated that suspending agents with long chain hydrocarbyls having $C_8$—$O_{22}$ chains may be used. Other long chain acyl derivatives suitable for use as suspending agents include N,N-dihydrocarbyl amido benzoic acid and soluble salts thereof (e.g. Na, K), particularly N,N-di(hydrogenated) C16, C18 and tallow amido benzoic acid species of this family, which are commercially available from Stepan Company (Northfield, Ill., USA). Examples of suitable long chain amine oxides for use as suspending agents include alkyl (C16-C22) dimethyl amine oxides, e.g. stearyl dimethyl amine oxide. Other suitable suspending agents include xanthan gum at concentrations ranging from about 0.3-3%, or 0.4-1.2%, by weight of the shampoo compositions. The use of xanthan gum as a suspending agent is described, for example, in U.S. Pat. No. 4,788,006, which is expressly incorporated herein by reference in one or more non-limiting embodiments. Combinations of long chain acyl derivatives and xanthan gum may also be used as a suspending agent in the shampoo compositions. Such combinations are described in U.S. Pat. No. 4,704,272, which is expressly incorporated herein by reference in one or more non-limiting embodiments. Other suitable suspending agents include carboxyvinyl polymers. Typical among these polymers are the copolymers of acrylic acid crosslinked with polyallylsucrose as described in U.S. Pat. No. 2,798,053, which is expressly incorporated herein by reference in one or more non-limiting embodiments. Examples of these polymers include Carbopol 934, 940, 941, and 956, available from B.F. Goodrich Company. Other suitable suspending agents include primary amines having a fatty alkyl moiety having at least 16 carbon atoms, examples of which include palmitamine or stearamine, and secondary amines having two fatty alkyl moieties each having at least 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer. Other suitable suspending agents may be used in the shampoo compositions, including those that can impart a gel-like viscosity to the composition, such as water soluble or colloidally water soluble polymers like cellulose ethers (e.g. methylcellulose, hydroxybutyl methylcellulose, hyroxypropylcellulose, hydroxypropyl methylcellulose, hydroxyethyl ethylcellulose and hydroxyethylcellulose), guar gum, polyvinyl alcohol, polyvinyl pyrrolidone, hydroxypropyl guar gum, starch and starch derivatives, and other thickeners, viscosity modifiers, gelling agents, etc.

The personal care composition, emulsion, film, aminosiloxane polymer, and/or any other composition described above, may include one or more water-soluble emollients including, but not limited to, lower molecular weight aliphatic diols, such as propylene glycol and butylene glycol; polyols, such as glycerine and sorbitol; and polyoxyethylene polymers, such as polyethylene glycol 200. The specific type and amount of water soluble emollient(s) employed will vary depending on the desired aesthetic characteristics of the composition, and is readily determined by one skilled in the art.

The personal care composition, emulsion, film, aminosiloxane polymer, and/or any other composition described above, may include one or more oils independent from the carrier fluid described above. The term "oil" as used herein describes any material which is substantially insoluble in water. Suitable oils include, but are not limited to, natural oils, such as coconut oil; hydrocarbons, such as mineral oil and hydrogenated polyisobutene; fatty alcohols, such as octyldodecanol; esters, such as $C_{12}$-$C_{15}$ alkyl benzoate;

diesters, such as propylene dipelarganate; and triesters, such as glyceryl trioctanoate and silicones especially cyclomethicone and dimethicone and combinations thereof. Suitable low viscosity oils have a viscosity of 5-100 mPas at 25° C., and are generally esters having the structure RCO—OR' wherein RCO represents the carboxylic acid radical and wherein OR' is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, or combinations thereof. The high viscosity surface oils generally have a viscosity of about 200-1,000,000, or 100,000-250,000, mPas at 25° C. Surface oils include castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof. The suggested ratio of low viscosity to high viscosity oils in the oil phase is about 1:15 to 15:1, or 1:10 to 10:1, respectively. The typical formulation of the disclosure includes about 1-20% of a combination of low viscosity and high viscosity surface oils.

Mineral oils, such as liquid paraffin or liquid petroleum, or animal oils, such as perhydrosqualene or arara oil, or alternatively of vegetable oils, such as sweet almond, calophyllum, palm, castor, avocado, jojoba, olive or cereal germ oil, may be utilized. It is also possible to use esters of lanolic acid, of oleic acid, of lauric acid, of stearic acid or of myristic acid, for example; alcohols, such as oeyl alcohol, linoleyl or linolenyl alcohol, isostearyl alcohol or octyldodecanol; or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

The personal care composition, emulsion, film, aminosiloxane polymer, and/or any other composition described above, may include various waxes. The waxes generally have a melting point of from 35-120° C. at atmospheric pressure. Waxes in this category include synthetic wax, ceresin, paraffin, ozokerite, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, or combinations thereof. In one embodiment, the personal care composition includes about 10-30% of a combination of waxes. Mention may be made, among the waxes capable of being used as non-silicone fatty substances, of animal waxes, such as beeswax; vegetable waxes, such as carnauba, candelilla, ouricury or japan wax or cork fibre or sugarcane waxes; mineral waxes, for example paraffin or lignite wax or microcrystalline waxes or ozokerites; synthetic waxes, including polyethylene waxes, and waxes obtained by the Fischer-Tropsch synthesis. Mention may be made, among the silicone waxes, of polymethylsiloxane alkyls, alkoxys and/or esters.

The personal care composition, emulsion, film, aminosiloxane polymer, and/or any other composition described above, may include a powder. The powder can be generally defined as dry, particulate matter having a particle size of 0.02-50 microns. The powder may be colored or non-colored (for example white). Suitable powders include bismuth oxychloride, titanated mica, fumed silica, spherical silica beads, polymethylmethacrylate beads, micronized teflon, boron nitride, acrylate polymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium carbonate, magnesium hydroxide, magnesium oxide, magnesium silicate, magnesium trisilicate, maltodextrin, montmorillonite, microcrystalline cellulose, rice starch, silica, talc, mica, titanium dioxide, zinc laurate, zinc myristate, zinc neodecanoate, zinc rosinate, zinc stearate, polyethylene, alumina, attapulgite, calcium carbonate, calcium silicate, dextran, kaolin, nylon, silica silylate, silk powder, serecite, soy flour, tin oxide, titanium hydroxide, trimagnesium phosphate, walnut shell powder, or combinations thereof. The powder may be surface treated with lecithin, amino acids, mineral oil, silicone oil, or various other agents either alone or in combination, which coat the powder surface and render the particles hydrophobic in nature.

The powder can also include or be an organic and/or inorganic pigment. Organic pigments are generally various aromatic types including azo, indigoid, triphenylmethane, anthraquinone, and xanthine dyes which are designated as D&C and FD&C blues, browns, greens, oranges, reds, yellows, etc. Inorganic pigments generally consist of insoluble metallic salts of certified color additives, referred to as the Lakes or iron oxides. A pulverulent coloring agent, such as carbon black, chromium or iron oxides, ultramarines, manganese pyrophosphate, iron blue, and titanium dioxide, pearlescent agents, generally used as a combination with colored pigments, or some organic dyes, generally used as a combination with colored pigments and commonly used in the cosmetics industry, can be added to the composition. In general, these coloring agents can be present in an amount by weight from 0-20% with respect to the weight of the personal care composition, emulsion, film, aminosiloxane polymer, and/or any other composition described above.

Pulverulent inorganic or organic fillers can also be added, generally in an amount by weight from 0-40% with respect to the weight of the personal care composition, emulsion, film, aminosiloxane polymer, and/or any other composition described above. These pulverulent fillers can be chosen from talc, micas, kaolin, zinc or titanium oxides, calcium or magnesium carbonates, silica, spherical titanium dioxide, glass or ceramic beads, metal soaps derived from carboxylic acids having 8-22 carbon atoms, non-expanded synthetic polymer powders, expanded powders and powders from natural organic compounds, such as cereal starches, which may or may not be crosslinked. The fillers may typically be present in a proportion of from 0-35, or 5-15, % of the total weight of the composition. Mention may be made in particular of talc, mica, silica, kaolin, nylon powders (in particular ORGASOL), polyethylene powders, Teflon, starch, boron nitride, copolymer microspheres, such as EXPANCEL (Nobel Industrie), polytrap and silicone resin microbeads (TOSPEARL from Toshiba, for example).

The personal care composition, emulsion, film, aminosiloxane polymer, and/or any other composition described above, may include a sunscreen. Sunscreens typically absorb ultraviolet light between 290-320 nanometers (the UV-B region) such as, but not exclusively, para-aminobenzoic acid derivatives and cinnamates, such as octyl methoxycinnamate and those which absorb ultraviolet light in the range of 320-400 nanometers (the UV-A region), such as benzophenones and butyl methoxy dibenzoylmethane. Some additional examples of sunscreens are 2-ethoxyethyl p-methoxycinnamate; menthyl anthranilate; homomethyl salicylate; glyceryl p-aminobenzoate; isobutyl p-aminobenzoate; isoamyl p-dimethylaminobenzoate; 2-hydroxy-4-methoxybenzophenones sulfonic acid; 2,2'-dihydroxy-4-methoxybenzophenone; 2-hydroxy-4-methoxybenzophenone; 4-mono and 4-bis(3-hydroxy-propyl)amino isomers of ethyl benzoate; and 2-ethylhexyl p-dimethylaminobenzoate. In various embodiments, the sunscreen is as described in EP-A-678, 292, which is expressly incorporated herein by reference in one or more non-limiting embodiments. In various embodiments, sunscreens include at least one carboxylic or better still sulphonic acid radical. This acid radical can be in free form or in partially or totally neutralized form. It is possible to use one or more hydrophilic screening agents containing acid functionality. As examples of acidic screening agents containing at least one $SO_3H$ group, mention may be made more particularly of 3-benzylidine-2-camphorsulphonic derivatives. A particularly typical compound is benzene-1, 4-[di(3-methylidenecamphor-10-sulphonic acid)]. This screening agent is a broad-band screening agent capable of absorbing ultraviolet rays with wavelengths of between 280 nm and 400 nm, with absorption maxima of between 320 nm and 400 nm, in particular at 345 nm. It is used in acid form or salified with a base chosen from triethanolamine, sodium hydroxide and potassium hydroxide. In addition, it can be in cis or trans form. This screening agent is known under the trade name Mexoryl SX. Other specific examples are 4-(3-methylidenecamphor)benzenesulphonic acid, 3-benzylidenecamphor-10-sulphonic acid, 2-methyl-5-(3-methylidenecamphor)benzenesulphonic acid, 2-chloro-5-(3-methylidenecamphor)benzenesulphonic acid, 3-(4-methyl)benzylidenecamphor-10-sulphonic acid, (3-t-butyl-2-hydroxy-5-methyl)benzylidenecamphor-10-sulphonic acid, (3-t-butyl-2-hydroxy-5-methoxy)benzylidenecamphor-10-sulphonic acid, (3,5-di-tert-butyl-4-hydroxy)benzylidenecamphor-10-sulphonic acid, 2-methoxy-5-(3-methylidenecamphor)benzenesulphonic acid, 3-(4,5-methylenedioxy)benzylidenecamphor-10-sulphonic acid, 3-(4-methoxy)benzylidenecamphor-10-sulphonic acid, 3-(4,5-dimethoxy)benzylidenecamphor-10-sulphonic acid, 3-(4-n-butoxy)benzylidenecamphor-10-sulphonic acid, 3-(4-n-butoxy-5-methoxy)benzylidenecamphor-10-sulphonic acid, 2-[4-(camphormethylidene)phenyl]benzimidazole-5-sulphonic acid. Suitable compounds are described in U.S. Pat. No. 4,585,597, and FR 2,236,515, 2,282,426, 2,645,148, 2,430, 938 and 2,592,380, each of which is expressly incorporated herein by reference in one or more non-limiting embodiments. The screening agent containing a sulphonic group can also be a sulphonic derivative of benzophenone or 2-phenylbenzimidazole-5-sulphonic acid, having excellent photoprotective power in the UV-B radiation range and is sold under the trade name "Eusolex 232" by Merck, benzene-1,4-di(benzimidazol-2-yl-5-sulphonic acid), benzene-1,4-di(benzoxazol-2-yl-5-sulphonic acid). The hydrophilic screening agent(s) can be present in the final composition according to the disclosure in a content which can be from about 0.1-20%, or 0.2-10%, by weight relative to the total weight of the personal care composition.

Additional lipophilic screening agents can be utilized, such as those derived from dibenzoylmethane and more especially 4-tert-butyl-4'-methoxydibenzoylmethane, which effectively have a high intrinsic power of absorption. These dibenzoylmethane derivatives, which are products that are well known per se as UV-A active screening agents, are described in particular in French patent applications FR-A-2,326,405 and FR-A-2,440,933, as well as in European patent application EP-A-0,114,607, each of which is expressly incorporated herein by reference in one or more non-limiting embodiments. 4-(tert-butyl)-4'-methoxydibenzoylmethane is currently sold under the trade name "Parsol 1789" by Givaudan. Another dibenzoylmethane derivative which is typical according to the present disclosure is 4-isopropyldibenzoylmethane, this screening agent being sold under the name "Eusolex 8020" by Merck. Similarly octocrylene, a liquid lipophilic screening agent that is already known for its activity in the UV-B range is commercially available, and is sold in particular under the name "Uvinul N 539" by BASF. As another lipophilic (or liposoluble) screening agent which can be used in the disclosure, mention may also be made of p-methylbenzylidenecamphor, which is also known as a UV-B absorber and is sold in particular under the trade name "Eusolex 6300" by Merck. The lipophilic screening agent(s) can be present in the composition according to the disclosure in a content which can be from about 0.5-30%, or 0.5-20%, of the total weight of the personal care composition, emulsion, film, aminosiloxane polymer, and/or any other composition described above. Other examples of lipophilic or hydrophilic organic screening agents are described in patent application EP-A-0,487,404, which is expressly incorporated herein by reference in one or more non-limiting embodiments. The cosmetic and/or dermatological compositions according to the disclosure can also include pigments or alternatively nano-pigments (average primary particle size: generally between 5-100, or 10-50, nm) of coated or uncoated metal oxides, such as, for example, nano-pigments of titanium oxide (amorphous or crystallized in rutile and/or anatase form), of iron oxide, of zinc oxide, of zirconium oxide or of cerium oxide, which are all photoprotective agents that are well known per se and which act by physically blocking (reflection and/or scattering) UV radiation. Standard coating agents are, moreover, alumina and/or aluminum stearate, and silicones. Such coated or uncoated metal oxide nano-pigments are described in particular in patent applications EP-A-0,518,772 and EP-A-0,518,773, each of which is expressly incorporated herein by reference in one or more non-limiting embodiments.

A thickening agent may be utilized to provide a convenient viscosity for any composition described above. For example, viscosities of from about 500-25,000, or 3,000-7, 000, $mm^2/s$ at 25° C. may be obtained. Suitable thickening agents are exemplified by sodium alginate, gum arabic, polyoxyethylene, guar gum, hydroxypropyl guar gum, ethoxylated alcohols, such as laureth-4 or polyethylene glycol 400, cellulose derivatives exemplified by methylcellulose, methylhydroxypropylcellulose, hydroxypropylcellulose, polypropylhydroxyethylcellulose, starch, and starch derivatives exemplified by hydroxyethylamylose and starch amylose, locust bean gum, electrolytes exemplified by sodium chloride and ammonium chloride, and saccharides, such as fructose and glucose, and derivatives of saccharides, such as PEG-120 methyl glucose diolate or combinations of 2 or more of these. Alternatively, the thickening agent is chosen from cellulose derivatives, saccharide derivatives, and electrolytes, or from a combination of two or more of the above thickening agents exemplified by a combination of a cellulose derivative and any electrolyte, and a starch derivative and any electrolyte. The thickening agent, where used is present in a shampoo composition, may provide a viscosity of from about 500-25,000 mm$^2$/s at 25° C. Alternatively, the thickening agent may be present in an amount from about 0.05-10, or 0.05-5, wt. % based on the total weight of the personal care composition, emulsion, film, aminosiloxane polymer, and/or any other composition described above.

Stabilizing agents can also be used, e.g. in a water phase of an emulsion. Suitable water phase stabilizing agents can include alone or in combination one or more electrolytes, polyols, alcohols, such as ethyl alcohol, and hydrocolloids. Typical electrolytes are alkali metal salts and alkaline earth salts, especially the chloride, borate, citrate, and sulfate salts of sodium, potassium, calcium and magnesium, as well as aluminum chlorohydrate, and polyelectrolytes, especially hyaluronic acid and sodium hyaluronate. When the stabilizing agent is, or includes, an electrolyte, it amounts to about 0.1-5, or 0.5-3, wt. % of the personal care composition, emulsion, film, aminosiloxane polymer, and/or any other composition described above. The hydrocolloids include gums, such as Xantham gum or Veegum and thickening agents, such as carboxymethyl cellulose. Polyols, such as glycerine, glycols, and sorbitols can also be used. Alternative polyols are glycerine, propylene glycol, sorbitol, and butylene glycol. If a large amount of a polyol is used, one need not add the electrolyte. However, it is typical to use a combination of an electrolyte, a polyol and a hydrocolloid to stabilize the water phase, e.g. magnesium sulfate, butylene glycol and Xantham gum.

Any of the aforementioned compositions may also be or include antiperspirant agents and deodorant agents, such as Aluminum Chloride, Aluminum Zirconium Tetrachlorohydrex GLY, Aluminum Zirconium Tetrachlorohydrex PEG, Aluminum Chlorohydrex, Aluminum Zirconium Tetrachlorohydrex PG, Aluminum Chlorohydrex PEG, Aluminum Zirconium Trichlorohydrate, Aluminum Chlorohydrex PG, Aluminum Zirconium Trichlorohydrex GLY, Hexachlorophene, Benzalkonium Chloride, Aluminum Sesquichlorohydrate, Sodium Bicarbonate, Aluminum Sesquichlorohydrex PEG, Chlorophyllin-Copper Complex, Triclosan, Aluminum Zirconium Octachlorohydrate, and Zinc Ricinoleate.

The personal care composition, emulsion, film, aminosiloxane polymer, and/or any other composition described above, can be an aerosol in combination with propellant gases, such as carbon dioxide, nitrogen, nitrous oxide, volatile hydrocarbons, such as butane, isobutane, or propane and chlorinated or fluorinated hydrocarbons, such as dichlorodifluoromethane and dichlorotetrafluoroethane or dimethylether.

Silicone compositions, other than the present aminosiloxane polymer may also be included in the personal care composition, emulsion, film, aminosiloxane polymer, and/or any other composition described above. For example, such silicones include silicone fluids, gums, resins, elastomers; silicone surfactants and emulsifiers, such as silicone polyethers, organofunctional silicones, such as amino functional silicones and alkylmethylsiloxanes. Alkylmethylsiloxanes may be included in the present compositions. These siloxane polymers generally typically have the formula Me$_3$SiO[Me$_2$SiO]$_y$[MeRSiO]$_z$SiMe$_3$, in which R is a hydrocarbon group containing 6-30 carbon atoms, Me represents methyl, and the Dp (i.e., the sum of "y" and "z") is 3-50. Both the volatile and liquid species of alkylmethysiloxanes can be used in the composition.

Silicone gums may also be included in the personal care composition, emulsion, film, aminosiloxane polymer, and/or any other composition described above. Suitable non-limiting gums include insoluble polydiorganosiloxanes having a viscosity >1,000,000 centistoke (mm2/s) at 25° C., alternatively >5,000,000 centistoke (mm$^2$/s) at 25° C. These silicone gums are typically sold as compositions already dispersed in a suitable solvent to facilitate their handling. Ultra-high viscosity silicones can also be included as optional ingredients. These ultra-high viscosity silicones typically have a kinematic viscosity >5 million centistoke (mm$^2$/s) at 25° C. up to 20 million centistoke (mm$^2$/s) at 25° C. Compositions of this type in are described for example in U.S. Pat. No. 6,013,682, which is expressly incorporated herein by reference in one or more non-limiting embodiments.

Silicone resins may also be included in the personal care composition, emulsion, film, aminosiloxane polymer, and/or any other composition described above. These resins are generally highly crosslinked polymeric siloxanes. Crosslinking is typically obtained by incorporating trifunctional and/or tetrafunctional silanes with the monofunctional silane and/or difunctional silane monomers used during manufacture. The degree of crosslinking required to obtain a suitable silicone resin will vary according to the specifics of silane monomer units incorporated during manufacture of the silicone resin. In general, any silicone having a sufficient level of trifunctional and tetrafunctional siloxane monomer units, and hence possessing sufficient levels of crosslinking to dry down to a rigid or a hard film can be used. Commercially available silicone resins suitable for applications herein are generally supplied in an unhardened form in low viscosity, volatile or nonvolatile silicone fluids. The silicone resins may be incorporated into compositions of the disclosure in their non-hardened forms rather than as hardened resinous structures.

Silicone carbinol fluids may be included in the personal care composition, emulsion, film, aminosiloxane polymer, and/or any other composition described above. These materials can be commonly described as substituted hydrocarbyl functional siloxane fluids or resins and some are described in WO 03/101412 A2, which is expressly incorporated herein by reference in one or more non-limiting embodiments.

Water soluble or water dispersible silicone polyethers may also be included in the personal care composition, emulsion, film, aminosiloxane polymer, and/or any other composition described above. These are also known as polyalkylene oxide silicone copolymers, silicone poly(oxyalkylene) copolymers, silicone glycol copolymers, or silicone surfactants. These can be linear rake or graft type materials, or ABA type where the B is the siloxane polymer block, and the A is the poly(oxyalkylene) group. The poly (oxyalkylene) group can consist of polyethylene oxide, polypropylene oxide, or mixed polyethylene oxide/polypropylene oxide groups. Other oxides, such as butylene oxide or phenylene oxide are also possible.

Any of the personal care composition, emulsion, film, aminosiloxane polymer, and/or any other composition described above may also include a solvent, such as (i) organic compounds, (ii) compounds containing a silicon atom, (iii) mixtures of organic compounds, (iv) mixtures of compounds containing a silicon atom, or (v) mixtures of organic compounds and compounds containing a silicon atom; used on an industrial scale to dissolve, suspend, or change the physical properties of other materials.

In general, the organic compounds are aromatic hydrocarbons, aliphatic hydrocarbons, alcohols, aldehydes, ketones, amines, esters, ethers, glycols, glycol ethers, alkyl halides, or aromatic halides. Representative of some common organic solvents are alcohols, such as methanol, ethanol, 1-propanol, cyclohexanol, benzyl alcohol, 2-octanol, ethylene glycol, propylene glycol, and glycerol; aliphatic hydrocarbons, such as pentane, cyclohexane, heptane, VM&P solvent, and mineral spirits; alkyl halides, such as chloroform, carbon tetrachloride, perchloroethylene, ethyl chloride, and chlorobenzene; amines, such as isopropylamine, cyclohexylamine, ethanolamine, and diethanolamine; aromatic hydrocarbons, such as benzene, toluene, ethylbenzene, and xylene; esters, such as ethyl acetate, isopropyl acetate, ethyl acetoacetate, amyl acetate, isobutyl isobutyrate, and benzyl acetate; ethers, such as ethyl ether, n-butyl ether, tetrahydrofuran, and 1,4-dioxane; glycol ethers, such as ethylene glycol monomethyl ether, ethylene glycol monomethyl ether acetate, diethylene glycol monobutyl ether, and propylene glycol monophenyl ether; ketones, such as acetone, methyl ethyl ketone, cyclohexanone, diacetone alcohol, methyl amyl ketone, and diisobutyl ketone; petroleum hydrocarbons, such as mineral oil, gasoline, naphtha, kerosene, gas oil, heavy oil, and crude oil; lubricating oils, such as spindle oil and turbine oil; and fatty oils, such as corn oil, soybean oil, olive oil, rapeseed oil, cotton seed oil, sardine oil, herring oil, and whale oil.

"Other" miscellaneous organic solvents can also be used, such as acetonitrile, nitromethane, dimethylformamide, propylene oxide, trioctyl phosphate, butyrolactone, furfural, pine oil, turpentine, and m-creosol.

Solvents may also include volatile flavoring agents, such as oil of wintergreen; peppermint oil; spearmint oil; menthol; vanilla; cinnamon oil; clove oil; bay oil; anise oil; eucalyptus oil; thyme oil; cedar leaf oil; oil of nutmeg; oil of sage; cassia oil; cocoa; licorice; high fructose corn syrup; citrus oils, such as lemon, orange, lime, and grapefruit; fruit essences, such as apple, pear, peach, grape, strawberry, raspberry, cherry, plum, pineapple, and apricot; and other useful flavoring agents including aldehydes and esters, such as cinnamyl acetate, cinnamaldehyde, eugenyl formate, p-methylanisole, acetaldehyde, benzaldehyde, anisic aldehyde, citral, neral, decanal, vanillin, tolyl aldehyde, 2,6-dimethyloctanal, and 2-ethyl butyraldehyde.

Moreover, solvents may include volatile fragrances, such as natural products and perfume oils. Some representative natural products and perfume oils are ambergris, benzoin, civet, clove, leaf oil, jasmine, mate, mimosa, musk, myrrh, orris, sandalwood oil, and vetivert oil; aroma chemicals, such as amyl salicylate, amyl cinnamic aldehyde, benzyl acetate, citronellol, coumarin, geraniol, isobornyl acetate, ambrette, and terpinyl acetate; and the various classic family perfume oils, such as the floral bouquet family, the oriental family, the chypre family, the woody family, the citrus family, the canoe family, the leather family, the spice family, and the herbal family.

Other components that may be used for purposes of this disclosure are described in PCT/US15/024905 and PCT/US15/024886, each of which is expressly incorporated herein by reference in one or more non-limiting embodiments. The following examples are intended to illustrate and not to limit the invention.

EXAMPLES

Example 1: Preparation of Intermediate

To a 16 oz. jar, the following components were charged: 8.48 g of maleic anhydride (Sigma Aldrich® Lot BCBG7375V), 11.52 g of N,N-Diisopropanolamine (Sigma Aldrich® Lot 1434040) and 40.00 g HPLC grade acetone to create a 33.3% active solution. The reaction is carried out under ambient conditions on a magnetic stir plate. The reaction is exothermic and causes acetone to boil as amidation occurs. The solution quickly changes from optically clear to pale yellow.

The intermediate structure was confirmed by $^1$H NMR in d4-methanol. Representative peaks which confirm intended reaction are found at $\delta=3.72$ ppm; the protons next to the amido nitrogen, $\delta=6.8$ ppm; as set forth in the bottom spectra of FIG. 1.

Example 2: Michael Addition of Polyorganosiloxane and Intermediate

Figure 2:
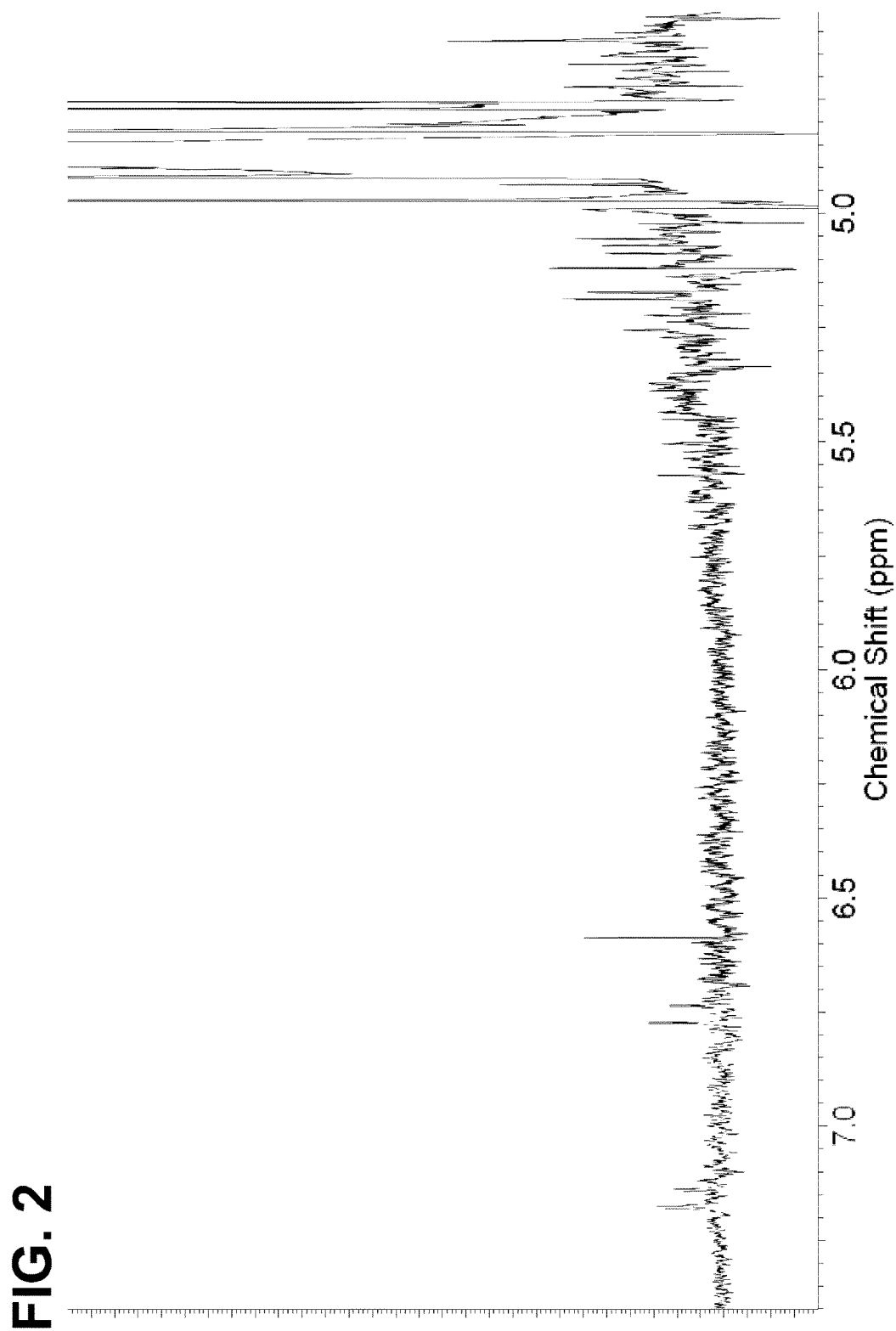
FIG. 2 is a $^1$H NMR spectrograph of Example 2.

To an 8 oz. vial, the following components were charged: 1.50 g of 3-aminopropyl-heptamethyltrisiloxane and 0.50 g of the intermediate of Example 1 at a concentration of 70% (w/w) in HPLC grade acetone. The reaction vessel was charged with a magnetic stir bar and placed in an 80° C. water bath with mechanical agitation for a 5 hour period. After the reaction was deemed complete, the product was diluted 1:10 (w/w) in d4-methanol and elucidated by 1H NMR, as shown in FIG. 2. This spectra shows the disappearance of the C=C bond (absence of proton NMR peaks at 6.8) and the formation of the methylene H groups (H NMR peak at 4.52)

Example 3: Michael Addition of Polyorganosiloxane and Intermediate

To a 250 mL flask, the following components were charged: 94.45 g of a 300 Dp 3-aminopropypolydimethylsiloxane of about 2 mol % amine and 6.97 g of the aforementioned intermediate at a concentration of 87% (w/w) in deionized water. The reaction vessel was charged with a magnetic stir bar and placed in a 80° C. water bath with mechanical agitation for a 5 hour period. After the reaction was deemed completed, the product was evaluated for viscosity on an Ares® rheometer of from 1,500 cP to about 800,000 cP. The reason there is no NMR data is due to the low concentration of the C=C originating from dilution of the intermediate by the siloxane to below the NMR detection threshold. Instead, high viscosity is observed to show success.

Example 4: Michael Addition of Polyorganosiloxane and Intermediate in Emulsion 10 g of aminopropylaminoisobutysiloxane of about 400 Dp and 2 mol % of amine was emulsified to a 50 gram emulsion. After formation of the emulsion, 50 g of the emulsion was combined with 2.0 g of the intermediate (90 wt. % in water) to form a second emulsion. The second emulsion was mixed at room temperature for 20 min and then at 70° C. for 12 hours. A polymer internal phase was harvested by breaking the second emulsion with methanol and hexanes. The viscosity of the polymer increased from about 2,300 to 140,000 cP as measured by the Ares® controlled stress-rheometer.

The terms "comprising" or "comprise" are used herein in their broadest sense to mean and encompass the notions of "including", "include", "consist(ing) essentially of", and "consist(ing) of". The use of "for example", "e.g.", "such as", and "including" to list illustrative examples does not limit to only the listed examples. Thus, "for example" or "such as" means "for example, but not limited to" or "such as, but not limited to" and encompasses other similar or equivalent examples. The term "about" as used herein serves to reasonably encompass or describe minor variations in numerical values measured by instrumental analysis or as a result of sample handling. Such minor variations may be in the order of ±0-10, ±0-5, or ±0-2.5, % of the numerical values. Further, The term "about" applies to both numerical values when associated with a range of values. Moreover, the term "about" may apply to numerical values even when not explicitly stated.

Generally, as used herein a hyphen "-" or dash "—" in a range of values is "to" or "through"; a ">" is "above" or "greater-than"; a "≥" is "at least" or "greater-than or equal to"; a "<" is "below" or "less-than"; and a "≤" is "at most" or "less-than or equal to". On an individual basis, each of the aforementioned applications for patent, patents, and/or patent application publications, is expressly incorporated herein by reference in its entirety in one or more non-limiting embodiments.

One or more of the values described above may vary by ±5%, ±10%, ±15%, ±20%, ±25%, etc. so long as the variance remains within the scope of the disclosure. Unexpected results may be obtained from each member of a Markush group independent from all other members. Each member may be relied upon individually and or in combination and provides adequate support for specific embodiments within the scope of the appended claims. The subject matter of all combinations of independent and dependent claims, both single and multiple dependent, is herein expressly contemplated. It is contemplated that any and all values or ranges of values between those described above may also be utilized. Moreover, all combinations of all chemistries, compounds, and concepts described above, and all values of subscripts and superscripts described above, are expressly contemplated in various non-limiting embodiments. The disclosure is illustrative including words of description rather than of limitation. Many modifications and variations of the present disclosure are possible in light of the above teachings, and the disclosure may be practiced otherwise than as specifically described herein.

What is claimed is:

1. An aminosiloxane polymer comprising at least one Si-bonded functional group having the chemical formula:

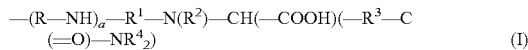

wherein R is a $C_1$-$C_{10}$ hydrocarbon group; $R^1$ is a $C_1$-$C_{10}$ hydrocarbon group; $R^2$ is a hydrogen atom, a $C_1$-$C_{12}$ hydrocarbon group, or a phenyl group; $R^3$ is a $C_1$-$C_4$ hydrocarbon group; each $R^4$ is independently a hydrogen atom, a $C_1$-$C_{12}$ hydrocarbon group, a $C_1$-$C_{12}$ hydroxyl-hydrocarbon group, or a phenyl group; and "a" is 0 or 1.

2. The aminosiloxane polymer of claim 1 that is the reaction product of:
(A) a polyorganosiloxane having an amino group; and
(B) a reaction product of; i) an alkylamine and/or alkanolamine, and ii) an alkenyl cyclic anhydride.

3. The aminosiloxane polymer of claim 2, wherein said (A) polyorganosiloxane having the amino group has the chemical structure:

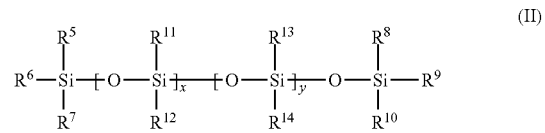

wherein each of $R^5$, $R^6$, $R^7$, $R^8$, $R^9$, $R^{10}$, $R^{11}$, $R^{12}$, and $R^{13}$ is independently OH, R'(OR")$_m$ or R'OH, where "m" is 1 to 3, and each of R' and R" is independently an alkyl group, a $C_1$-$C_{12}$ hydrocarbon group, a $C_2$-$C_{30}$ alkenyl group, a $C_6$-$C_{12}$ aromatic group, or a polyalkyleneoxy group; "x" is from 1 to 3,000; "y" is from 1 to 100; and $R^{14}$ comprises the amino group.

4. The aminosiloxane polymer of claim 2, wherein said amino group of component (A) comprises:
i) a $NH_2$ moiety bonded to a linear, branched, or cyclic hydrocarbon having 1 to 6 carbon atoms and said linear, branched, or cyclic hydrocarbon is bonded to a Si atom of component (A); or
ii) one or more $NH_2$, NH, or NHR', moieties, where R' is an alkyl group.

5. The aminosiloxane polymer of claim 2, wherein:
i) said alkylamine of component (B) comprises at least one NH moiety and at least one carbon chain having 3 to 12 carbon atoms;
ii) said alkanolamine of component (B) comprises one or two hydroxyl groups; or
iii) both i) and ii).

6. The aminosiloxane polymer of claim 1, wherein said Si-bonded functional group has the chemical structure:

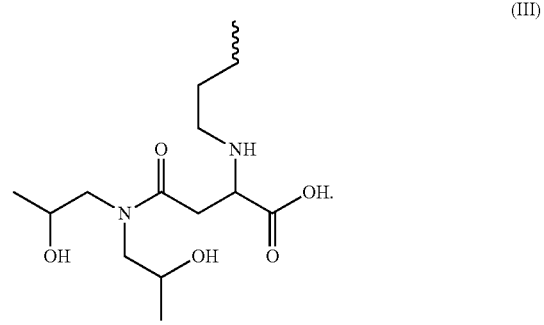

7. The aminosiloxane polymer of claim 1, having the chemical structure:

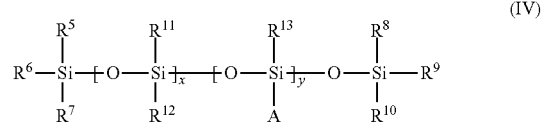

wherein each of $R^5$, $R^6$, $R^7$, $R^8$, $R^9$, $R^{10}$, $R^{11}$, $R^{12}$, and $R^{13}$ is independently OH, R'(OR")$_m$, or R'OH, where "m" is 1 to 3, and each of R' and R" is independently an alkyl group, a $C_1$-$C_{12}$ hydrocarbon group, a $C_2$-$C_{30}$ alkenyl group, a $C_6$-$C_{12}$ aromatic group, or a polyalkyleneoxy group; "x" is from 1 to 3,000; "y" is from 1 to 100; and "A" is said Si-bonded functional group.

8. An emulsion comprising:
I) a liquid continuous phase; and
II) a dispersed phase comprising an aminosiloxane polymer comprising at least one Si-bonded functional group having the chemical formula:

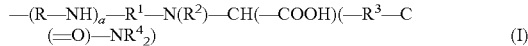

$$—(R—NH)_a—R^1—N(R^2)—CH(—COOH)(—R^3—C(=O)—NR^4{}_2) \quad (I)$$

wherein R is a $C_1$-$C_{10}$ hydrocarbon group; $R^1$ is a $C_1$-$C_{10}$ hydrocarbon group; $R^2$ is a hydrogen atom, a $C_1$-$C_{12}$ hydrocarbon group, or a phenyl group; $R^3$ is a $C_1$-$C_4$ hydrocarbon group; each $R^4$ is independently a hydrogen atom, a $C_1$-$C_{12}$ hydrocarbon group, a $C_1$-$C_{12}$ hydroxyl-hydrocarbon group, or a phenyl group; and "a" is 0 or 1.

9. The emulsion of claim 8, wherein said aminosiloxane polymer of said dispersed phase:
i) is a liquid; and/or
ii) is present as particles dispersed in said continuous phase and said dispersed particles have a size of less than about 15 µm; and/or
iii) is present in said emulsion in an amount of from 10 to 90 parts by weight per 100 parts by weight of said emulsion.

10. The emulsion of claim 8, further comprising a polydialkylsiloxane having a weight average molecular weight ($M_w$) of up to 1,000,000 g/mol, and wherein a ratio of said polydialkylsiloxane to said aminosiloxane polymer is from about 0.1 to 100.

11. A composition comprising the aminosiloxane polymer as set forth in claim 1, said composition chosen from personal care compositions, cosmetic compositions, fabric treating compositions, fiber treating compositions, hair care compositions, fiber care compositions, and combinations thereof.

12. A method of forming an aminosiloxane polymer comprising at least one Si-bonded functional group, said method comprising the steps of:
providing a polyorganosiloxane having an amino group;
providing an alkylamine and/or an alkanolamine;
providing an alkenyl cyclic anhydride;
reacting i) the alkylamine and/or alkanolamine and ii) the alkenyl cyclic anhydride to form an intermediate; and
reacting the intermediate and the polyorganosiloxane having the amino group to form the aminosiloxane polymer;
the Si-bonded functional group having the chemical formula:

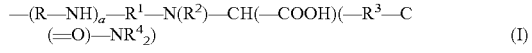

$$—(R—NH)_a—R^1—N(R^2)—CH(—COOH)(—R^3—C(=O)—NR^4{}_2) \quad (I)$$

wherein R is a $C_1$-$C_{10}$ hydrocarbon group; $R^1$ is a $C_1$-$C_{10}$ hydrocarbon group; $R^2$ is a hydrogen atom, a $C_1$-$C_{12}$ hydrocarbon group, or a phenyl group, $R^3$ is a $C_1$-$C_4$ hydrocarbon group; each $R^4$ is independently a hydrogen atom, $C_1$-$C_{12}$ hydrocarbon group, a $C_1$-$C_{12}$ hydroxyl-hydrocarbon group, or a phenyl group; and "a" is 0 or 1.

13. The method of claim 12, wherein the step of providing the polyorganosiloxane having the amino group is further defined as:
providing a first emulsion comprising a first continuous phase and a first dispersed phase comprising the polyorganosiloxane having the amino group;
wherein the step of reacting the intermediate and the polyorganosiloxane having the amino group is further defined as:
adding the intermediate to the first emulsion to form a second emulsion and heating the second emulsion to a temperature of about 20° C. to 80° C. to form the aminosiloxane polymer in-situ in the second emulsion; and
wherein the second emulsion comprises a second continuous phase and a second dispersed phase comprising the aminosiloxane polymer.

14. The method of claim 13, wherein the first dispersed phase and/or the second dispersed phase further comprise a polydialkylsiloxane having a weight average molecular weight ($M_w$) of up to 1,000,000 g/mol and a ratio of the polydialkylsiloxane to the aminosiloxane polymer is from about 0.1 to 100.

15. The method of claim 13, wherein:
i) the polyorganosiloxane having the amino group is present in the first dispersed phase of the first emulsion in an amount of from about 10 to 70 parts by weight per 100 parts by weight of the first emulsion; and/or
ii) the polyorganosiloxane having the amino group is present in the second dispersed phase of the second emulsion in an amount of from about 10 to 70 parts by weight per 100 parts by weight of the second emulsion; and/or
iii) the intermediate is present in the second dispersed phase of the second emulsion in an amount of from about 0.1 to 30 parts by weight per 100 parts by weight of the second emulsion.

16. The aminosiloxane polymer of claim 2, wherein:
i) said alkylamine of component (B) comprises at least one NH moiety and at least one carbon chain having 3 to 12 carbon atoms;
ii) said alkanolamine of component (B) comprises a single NH moiety and 2 to 5 hydroxyl groups; or
iii) both i) and ii).

17. The aminosiloxane polymer of claim 6, having the chemical structure:

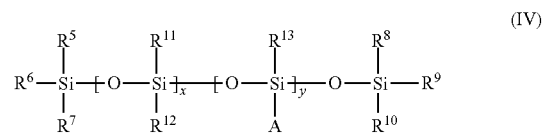

(IV)

wherein each of $R^5$, $R^6$, $R^7$, $R^8$, $R^9$, $R^{10}$, $R^{11}$, $R^{12}$, and $R^{13}$ is independently OH, R'(OR")$_m$, or R'OH, where "m" is 1 to 3, and each of R' and R" is independently an alkyl group, a $C_1$-$C_{12}$ hydrocarbon group, a $C_2$-$C_{30}$ alkenyl group, a $C_6$-$C_{12}$ aromatic group, or a polyalkyleneoxy group; "x" is from 1 to 3,000; "y" is from 1 to 100; and "A" is said Si-bonded functional group.

18. The emulsion of claim 9, further comprising a polydialkylsiloxane having a weight average molecular weight ($M_w$) of up to 1,000,000 g/mol, and wherein a ratio of said polydialkylsiloxane to said aminosiloxane polymer is from about 0.1 to 100.

19. A composition comprising the emulsion as set forth in claim 8, said composition chosen from personal care compositions, cosmetic compositions, fabric treating compositions, fiber treating compositions, hair care compositions, fiber care compositions, and combinations thereof.

20. The method of claim 13, wherein the second dispersed phase further comprises a polydialkylsiloxane having a weight average molecular weight ($M_w$) of up to 1,000,000 g/mol and a ratio of the polydialkylsiloxane to the aminosiloxane polymer is from about 0.1 to 100.

* * * * *